(12) United States Patent
Conboy et al.

(10) Patent No.: US 7,837,993 B2
(45) Date of Patent: Nov. 23, 2010

(54) METHODS AND COMPOSITIONS FOR REGENERATION OF AGED SKELETAL MUSCLE TISSUES

(75) Inventors: Irina M. Conboy, Stanford, CA (US); Michael J. Conboy, Stanford, CA (US); Thomas A. Rando, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/078,899

(22) Filed: Mar. 10, 2005

(65) Prior Publication Data
US 2005/0208027 A1 Sep. 22, 2005

Related U.S. Application Data

(60) Provisional application No. 60/554,693, filed on Mar. 19, 2004.

(51) Int. Cl.
| | | |
|---|---|---|
| A61K 39/395 | (2006.01) | |
| A61K 39/38 | (2006.01) | |
| A61K 39/00 | (2006.01) | |
| C12P 21/08 | (2006.01) | |
| C07K 14/00 | (2006.01) | |
| C07K 16/00 | (2006.01) | |
| C07K 17/00 | (2006.01) | |

(52) U.S. Cl. .............. 424/130.1; 424/184.1; 424/198.1; 530/387.1; 530/300
(58) Field of Classification Search ................. 435/377; 514/44; 424/93.1
See application file for complete search history.

(56) References Cited

U.S. PATENT DOCUMENTS

| | | | |
|---|---|---|---|
| 5,780,300 A * | 7/1998 | Artavanis-Tsakonas et al. .. | 435/377 |
| 6,723,561 B2 * | 4/2004 | Russell et al. ................ | 435/377 |
| 2005/0187179 A1 * | 8/2005 | Miele et al. .................... | 514/44 |

OTHER PUBLICATIONS

Agrawal et al. In situ cell therapy: novel targets, familiar challenges. Trends in Biotechnology (Feb. 2005) vol. 23 (2), pp. 78-83.*
Verma et al. Gene therapy-promises, problems and prospects, Nature, 1997, vol. 389, pp. 239-242.*
Rubanyi, G.M. The future of gene therapy. Molecularr Aspects of Medicine, 2001, vol. 22, pp. 113-142.*
Juengst, E.T. What next for human gene therapy? British Medical Journal, 2003, vol. 3326, pp. 1410-1411.*
Conboy et al. Notch-mediated restoration of regnerative potential to aged muscle. Science (2003) vol. 302, pp. 1575-1577, Science supporting online material pp. 1-12 and supplemental Figures 1-3.*
Lefaucheur et al. Muscle regneration following injury can be modified in vivo by immune neutralization of basic fibroblast growth factor, transforming gowth factor beta1 or insulin-like growth factor I. Journal of Neuroimmunology (1995) vol. 57, pp. 85-91.*
Negroni et al. Myogenic stem cells: Regeneration and cell therapy in human skeletal muscle. Pathologie Biologie (2006) vol. 54, pp. 100-108.*
Sinha-Hikim I, Cornford M, Gaytan H, Lee ML, Bhasin S. Effects of testosterone supplementation on skeletal muscle fiber hypertrophy and satellite cells in community-dwelling older men. J Clin Endocrinol Metab. Aug. 2006;91(8):3024-33. Epub May 16, 2006.*
Turk R, Sterrenburg E, de Meijer EJ, van Ommen GJ, den Dunnen JT, 't Hoen PA. Muscle regeneration in dystrophin-deficient mdx mice studied by gene expression profiling. BMC Genomics. Jul. 13, 2005;6:98.*
Sun H, Li L, Vercherat C, Gulbagci NT, Acharjee S, Li J, Chung TK, Thin TH, Taneja R. Stra13 regulates satellite cell activation by antagonizing Notch signaling. J Cell Biol. May 21, 2007;177(4):647-57. Epub May 14, 2007.*
Luo D, Renault VM, Rando TA. The regulation of Notch signaling in muscle stem cell activation and postnatal myogenesis.Semin Cell Dev Biol. Aug.-Oct. 2005;16(4-5):612-22.*
Miller, et al. (Dec. 3, 2003) Sage KE (Science of Ageing Knowledge Environment), 2003(48): p. pe34.*
Rones, et al. Serrate and Notch Specify Cell Fates in the Heart Field by Suppressing Cariodmyogenesis (2000) Development, 127(17): 3865-76.*
Iso, et al., "Notch Signalling in Vascular Development" (2003) Arteriosclerosis, Thrombosis, and Vascular Biology, 23(4): 543-53.*
Wilson, et al. "Cutting Edge: An Essential Role for Notch-1 in the Development of Both Thymus-Independent and -Dependent T cells in the Gut" (2000) The Journal of Immunology, 165: 5397-400, e.g., Abstract.*
Conboy et al., Notch Mediated Restoration of Regenerative Potential to Aged Muscle, Science. Nov. 28, 2003;302(5650):1575-7.
Conboy et al., Rejuvenation of Aged Progenitor Cells by Exposure to a Young Systemic Environment, Nature. Feb. 17, 2005;433(7027):760-4.
Geiger et al., The Aging of Lympho-Hematopoietic Stem Cells, 2002, Nature Immunology, 3:329-333.
Genbank Accession No. AB036931, Sakano,S., Human Delta-2, Notch Ligand Gene, Published Only in DataBase (2000), Oct. 2, 2000.
Genbank Accession No. AF003522, Gray,G.E. et al., Human Ligands of the Notch Receptor, Am. J. Pathol. 154 (3), 785-794 (1999), Apr. 24, 2000.
Genbank Accession No. AF029778, Deng,Y. et al., Characterization, Chromosomal Localization, and the Complete 30-Kb Dna Sequence of the Human JAGGED2 (JAG2) Gene, Genomics 63 (1), 133-138 (2000), Feb. 28, 2000.

(Continued)

Primary Examiner—Robert M Kelly
(74) Attorney, Agent, or Firm—Hozicevic, Field & Francis LLP; Pamela J. Sherwood

(57) ABSTRACT

The regenerative potential of aged stem cells is enhanced by activation of the Notch signaling pathway and/or inhibition of TGF-β signaling pathway. Stem cells in aged tissues are capable of proliferation and tissue regeneration, but in their native setting are not provided with the appropriate signals to do so. By administering tissue regenerating agents, organ stem/progenitor cells are provided with the appropriate signals to regenerate the corresponding differentiated tissues.

6 Claims, 13 Drawing Sheets

OTHER PUBLICATIONS

Genbank Accession No. AF196571, Han,W. et al., A Soluble Form of Human Delta-Like-1 Inhibits Differentiation of Hematopoietic Progenitor Cells, Blood 95 (5), 1616-1625 (2000), Oct. 25, 2000.

Genbank Accession No. AF279305, Mailhos,C. et al., DELTA4, An Endothelial Specific Notch Ligand Expressed At Sites of Physiological and Tumor Angiogenesis, Differentiation 69 (2-3), 135-144 (2001), Feb. 7, 2002.

Genbank Accession No. BC000218, Strausberg,R.L. et al., Generation and Initial Analysis of More Than 15,000 Full-Length Human and Mouse CDNA Sequences, Proc. Natl. Acad. Sci. U.S.A. 99 (26), 16899-16903 (2002), Jul. 15, 2006.

Genbank Accession No. HSU61276, Lindsell,C.E. et al., Jagged: A Mammalian Ligand That Activates NOTCH1, Cell 80 (6), 909-917 (1995), Apr. 24, 2000.

Sim et al., The Age-Related Decrease in CNS Remyelination Efficiency Is Attributable to an Impairment of Both Oligodendrocyte Progenitor Recruitment and Differentiation, J Neurosci. Apr. 1, 2002;22(7):2451-9.

* cited by examiner

METHODS AND COMPOSITIONS FOR REGENERATION OF AGED SKELETAL MUSCLE TISSUES

CROSS-REFERENCE TO RELATED APPLICATIONS

This application claims priority to U.S. provisional application 60/554,693, filed Mar. 19, 2004.

This invention was made with Government support under contracts NS40718 and NS36409 awarded by the National Institutes of Health. The Government has certain rights in this invention.

BACKGROUND OF THE INVENTION

Stem cells have a capacity both for self-renewal and the generation of differentiated cell types. This pluripotentiality makes stem cells unique. In addition to studying the important normal function of stem cells in the regeneration of tissues, researchers have further sought to exploit the potential of in situ and/or exogenous stem cells for the treatment of a variety of disorders. While early, embryonic stem cells have generated considerable interest, the stem cells resident in adult tissues may also provide an important source of regenerative capacity.

These somatic, or adult, stem cells are undifferentiated cells that reside in differentiated tissues, and have the properties of self-renewal and generation of differentiated cell types. The differentiated cell types may include all or some of the specialized cells in the tissue. For example, hematopoietic stem cells give rise to all hematopoietic lineages, but do not seem to give rise to stromal and other cells found in the bone marrow. Sources of somatic stem cells include bone marrow, blood, the cornea and the retina of the eye, brain, skeletal muscle, dental pulp, liver, skin, the lining of the gastrointestinal tract, and pancreas. Adult stem cells are usually quite sparse. Often they are difficult to identify, isolate, and purify. Often, somatic stem cells are quiescient until stimulated by the appropriate growth signals.

Progenitor or precursor cells are similar to stem cells, but are usually considered to be distinct by virtue of lacking the capacity for self-renewal. Researchers often distinguish precursor/progenitor cells from stem cells in the following way: when a stem cell divides, one of the two new cells is often a stem cell capable of replicating itself again. In contrast, when a progenitor/precursor cell divides, it can form more progenitor/precursor cells or it can form two specialized cells, neither of which is capable of replicating itself. Progenitor/precursor cells can replace cells that are damaged or dead, thus maintaining the integrity and functions of a tissue such as liver or brain.

Stem cells from bone marrow are widely studied. Currently, they are used clinically to restore various blood and immune components to the bone marrow via transplantation. There are two major types of stem cells found in bone: hematopoietic stem cells that form blood and immune cells, and stromal (mesenchymal) stem cells that normally form bone, cartilage, and fat. The restricted capacity of hematopoietic stem cells to grow in large numbers and remain undifferentiated in the culture dish is a major limitation to their broader use for research and transplantation studies.

Muscle tissue in adult vertebrates regenerates from reserve myoblasts called satellite cells. Satellite cells are distributed throughout muscle tissue and are mitotically quiescient in the absence of injury or disease. Following recovery from damage due to injury or disease or in response to stimuli for growth or hypertrophy, satellite cells reenter the cell cycle, proliferate and enter existing muscle fibers or undergo differentiation into multinucleate myotubes, which form new muscle fiber. The myoblasts ultimately yield replacement muscle fibers or fuse into existing muscle fibers, thereby increasing fiber girth by the synthesis of contractile apparatus components. This process is illustrated, for example, by the nearly complete regeneration that occurs in mammals following induced muscle fiber degeneration or injury; the muscle progenitor cells proliferate and fuse together regenerating muscle fibers.

An important aspect of stem cell biology is the effect of aging. Many tissues of the major organ systems are composed of long-lived cells that are normally replaced infrequently, if at all. Therefore, such cells persist for significant portions of a mammal's lifespan. The functional activity of these cells changes over time in a process that is generally referred to as aging and, as most age-related changes in cells result in reduced functional viability, this is harmful.

The aging of stem cell populations has been documented for a number of systems. For example, the hematopoietic stem cell population, while able to maintain normal blood cell counts throughout life, in old age can lack the functional reserves to produce large numbers of progeny. It has been shown by Geiger & Van Zant (2002) *Nature Immunology* 3:329-333 that the number of HSC and progenitor cells does not decline dramatically in old age, and may actually increase. It was suggested that the important effects of aging may be on stem cell quality rather than quantity.

The age-related decrease in central nervous system remyelination efficiency has been attributed to an impairment of oligodendrocyte progenitor cell recruitment and differentiation, Sim et al. (2002) *J. Neurosci.* 22(7):2451-9. The progenitor cell response during remyelination of focal, toxin-induced CNS demyelination in young and old rats was compared and found to be delayed with aged animals.

Similarly, there is a decline in muscle bulk and performance associated with normal aging, resulting from gradual loss of both motor nerves and muscle fibers during senescence. Although skeletal muscle has the capacity to regenerate itself, this process is not activated in the elderly. It has been suggested that age-related changes within skeletal muscle tissue and the host environment affect the proliferation and fusion of myoblasts in response to injury in old animals.

The adverse effects of aging include deterioration in the ability of somatic stem cells to regenerate differentiated cells in multiple different tissues. Methods of increasing the ability of aged stem cell to regenerate tissue are of enormous clinical interest.

SUMMARY OF THE INVENTION

Methods and compositions are provided for enhancing the regenerative potential of stem and/or progenitor cells that was lost due to the aging process or a disease by activation of the Notch receptor signaling pathway. It has been found that stem cells in aged tissues are capable of proliferation and tissue regeneration, but in their native setting are not provided with the appropriate signals to do so, due to a lack of activating factors, and/or to the presence of inhibitory factors. By administering agents that activate Notch and/or block inhibitory factors, stem/progenitor cells are provided with signals appropriate to regenerate differentiated cells derived from the stem/progenitor cells. Methods are also provided for screening of other agents that can improve the regeneration of tissues, through activation of the Notch signaling pathway.

In one embodiment of the invention, a subject who is in need of tissue regeneration, because tissue has deteriorated due to an injury, disease or aging is provided with an agent that activates the Notch signaling pathway. In another embodiment, a subject who is in need of tissue regeneration because tissue has deteriorated due to an injury, disease or aging is provided with an agent that blocks TGF-β activity. In a related embodiment, such a subject is provided with a combination of Notch activating agent and TGF-β blocking agent. The agent may be provided systemically or locally. Agents of interest include ligands that bind to the extracellular domain of Notch. Activation of Notch signaling in a stem/progenitor cell may involve re-entry into cell cycle; proliferation; and differentiation of progeny cells into appropriate specialized cells and tissues.

In some embodiments, the tissue is muscle tissue. Resident in muscle tissue are satellite cells, which are stem cells that ultimately give rise to muscle fibers. Satellite cells in aged muscle are capable of regeneration of tissue when the Notch signaling pathway is activated.

In another embodiment, the tissue is neural tissue, including hippocampal tissue, where neural stem cells are resident, and are activated by the methods of the invention. In another embodiment, the tissue is hematopoietic, and hematopoietic and/or mesenchymal stem cells are activated. In another embodiment, the tissue is liver tissue, including hepatocytes and liver stem cells.

A tissue regenerative agent, which may include one or both of Notch activating agent and TGFβ blocking agent may be provided in a pharmaceutical formulation suitable for administration to a patient. Formulations of interest include those that provide for substantial retention of the agent in the tissue of interest.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE SPECIFIC EMBODIMENTS

Figure 1:
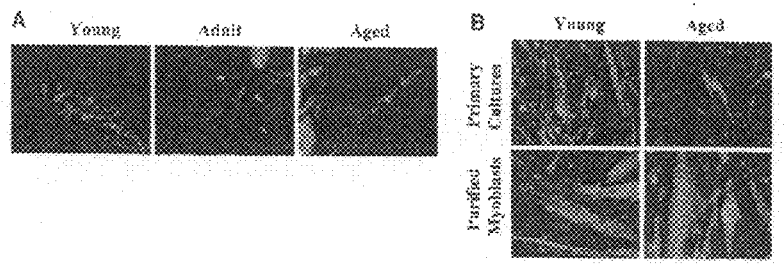
FIG. 1A-1B. Responses of satellite cell from mice of different ages. (A) Two days after muscle injury to young, adult, and aged mice, proliferating cells were labeled by intraperitoneal injections of 5-bromo-2' deoxyuridine (BrdU) 2 hours before muscle isolation. Dissociated myofiber fragments with associated cells were stained with a BrdU-specific antibody (red). As shown previously, nearly all myofiber-associated, BrdU$^+$ cells express myogenic markers such as M-cadherin or desmin, which confirms that they are derived from satellite cells. Hoechst costain (blue) labels nuclei. There were one-fourth to one-fifth as many BrdU$^+$ satellite cell derived myoblasts associated with myofibers from old mice as from young or adult mice (FIG. 5A; n≧3). (B) (Top) After 4 days ex vivo, cells from young and aged explant cultures were switched to differentiation medium to promote fusion and then stained with an antibody to embryonic myosin heavy chain (red) and with Hoechst dye. A marked decrease in the number of myotubes reflected the decreased myoblast production from old muscle. Results from adult cultures were similar to those shown for young cultures (see FIG. 5B). (Bottom) Young and aged myoblasts were adherence-purified, expanded, plated at equal numbers, and then cultured in differentiation medium. Under these conditions, myoblasts from aged mice fused to form myotubes as readily as did myoblasts from young mice (n≧3).

Methods and compositions are provided for enhancing the regenerative potential of stem and/or progenitor cells that was lost due to an aging process of a disease by activation of the Notch receptor signaling pathway. Stem cells in aged tissues are capable of proliferation and subsequent tissue regeneration, but lack the appropriate molecular signals. By administering agents that activate Notch, stem cells in tissues are induced to proliferate, thereby regenerating the tissue by providing appropriate numbers of cells that differentiate into the tissue of interest.

Aging tissues may also comprise factors that inhibit stem cell regeneration. In some embodiments of the invention, the effect of such inhibitors is diminished by the administration of an agent that blocks, or prevents the inhibitory activity. Exemplary of such factors is TGF-β.

A number of somatic stem/progenitor cells are known in the art, and benefit from the methods of the invention. These cells include satellite cells in muscle; hematopoietic stem cells; mesenchymal stem cells; neural stem cells; and the like.

In one embodiment of the invention, a subject in need of tissue regeneration is provided with an agent that activates the Notch signaling pathway. The agent may be provided systemically or locally. Agents of interest include ligands that bind to the extracellular domain of Notch. Activation of Notch signaling in a stem/progenitor cell may involve re-entry into cell cycle; proliferation; and differentiation of progeny cells into appropriate specialized cells and tissues. The Notch activating agent may be provided in a pharmaceutical formulation suitable for administration to a patient. Formulations may provide for targeting to a specific organ and retention of the agent in the tissue of interest. The methods, kits, and pharmaceutical compositions of the invention, by increasing stem cell activation, e.g. following tissue damage, significantly enhance the utility of presently available treatments for clinical treatments of the aged.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Tissue regenerative agent As used herein and as demonstrated in the Examples, agents that aid in the regeneration of aged stem cells include agents that activate the Notch signaling pathway; and agents that block activity of the TGFβ signaling pathway. One or both of said agents may be administered to a subject.

A determination of effective dose, and effective combination of agents may be determined empirically, for example using animal models as provided herein. In vitro models are also useful for the assessment of dose and selection of agent. For example, cultures are described herein where the regenerative potential of stem cells are evaluated in the absence or presence of serum from an individual where stem cell regeneration is comprised relative to a healthy young individual. Such cultures may be used to assay for the effectiveness of agents alone, or in combinations.

Notch. A tissue regenerative agent of interest for use in the methods of the invention may activate the Notch signaling pathway. As used herein, the terms "Notch" or "Notch gene product" or "Notch polypeptide" when used herein encompass native sequence Notch polypeptides, Notch polypeptide variants, Notch polypeptide fragments and chimeric Notch polypeptides. A "native sequence" polypeptide is one that has the same amino acid sequence as a Notch polypeptide derived from nature.

The term "native sequence Notch polypeptide" includes human Notch polypeptides. Human Notch proteins include the four different but related Notch genes (Notch 1; Notch 2, Notch 3, Notch 4), which show distinct spatio-temporal expression patterns. The genetic sequences of these proteins are known in the art, and may be accessed, for example, at public databases, including Genbank. Human Notch 1 has the Genbank accession number AF308602; human Notch 2 has the Genbank accession number AF308601.1; human Notch 3 has the Genbank accession number U97669; human Notch 4 has the Genbank accession number U95299. Notch 1 is of particular interest for muscle cells. Notch 1 and Notch 2 are expressed in hematopoietic stem cells; and Notch 1 has been implicated in HSC activation. Notch 2 and Notch 4 are of particular interest for neural cells.

Notch is a transmembrane protein with epidermal growth factor (EGF) repeats in the extracellular domain and ankyrin repeats in the intracellular domain. In addition to the EGF-like repeats in the extracellular region of Notch, known motifs in the intracellular region of Notch include a nuclear localization signal (NLS) and a RAM motif, 6 ankyrin/CDC10 repeats, a second NLS, PEST sequence, and a glutamine-rich domain. A highly conserved 109-amino acid region (residues 1773 to 1881) N-terminal to the 6 ankyrin repeats of intracellular NOTCH1 inhibits NFκB DNA binding and gene expression, which protein-protein interaction domain may be referred to as the NFκB-binding domain (NBD).

Although activation of most plasma membrane receptors ultimately leads to transcriptional changes, very few plasma membrane receptors can serve as both receptors and transcription factors. Notch receptors, the best characterized of this family, transduce signals primarily by nuclear translocation of a cleaved intracellular fragment. The Notch receptor is a heterodimer formed from its precursor following cleavage by a furin-like convertase. Cleavage occurs at an extracellular site, called site 1 (S1), after the recognition sequence RQRR. Notch can be activated by ligand binding. Among naturally occurring Notch ligands are Delta, Jagged, and Serrate. These ligands also have EGF repeats at the extracellular domain.

Activation of Notch 1 involves cleavage between gly1743 and val1744 (termed site 3, or 7). S3 cleavage serves to release the NOTCH1 intracellular domain (NICD) from the membrane. NICD then translocates to the nucleus, where it functions as a transcriptional activator in concert with CSL family members (CBF1, "suppressor of hairless", and LAG1), driving gene expression from Hes and Hey promoters. S3 processing occurs only in response to ligand binding. Ligand binding also facilitates cleavage at the S2 site within the extracellular juxtamembrane region. This serves to release ectodomain repression of NICD production. S2 cleavage occurs between ala1710 and val1711, approximately 12 amino acids outside the transmembrane domain. Cleavage at S2 generates a transient intermediate peptide termed NEXT (Notch extracellular truncation). NEXT accumulates when NICD production is blocked by point mutations or gamma-secretase inhibitors, or by loss of presenilin-1, and inhibition of NEXT eliminates NICD production.

Notch activating agents, or activators. Notch activators are agents that activate Notch signaling, usually through binding to the extracellular Notch domain, and subsequent processing steps as described above. Agents of interest may interact directly with Notch, e.g. antibodies, native ligands, synthetic ligands, and the like, or may activate downstream events. A number of Notch activators have been described and are known in the art. Activators may be specific for a Notch polypeptide, e.g. Notch 1, 2, 3 and/or 4; or may cross-react with one or more of the Notch polypeptides.

Among the known Notch activators are members of the Delta and Serrate/Jagged, gene families. These ligands share some structural features, including EGF-like repeats, a characteristic DSL domain necessary for Notch binding, and a transmembrane region. However, an extracellular cysteine-rich domain and insertions that interrupt some EGF-like repeats are common only to the Delta/Serrate family.

The genetic sequences of these proteins are known in the art, and may be accessed, for example, at public databases, including Genbank. Human Delta 1 has the Genbank accession number AF003522; Delta like 1 has the Genbank accession number AF196571; Delta 2 has the Genbank accession number AB036931; Delta-like 3 has the Genbank accession number BC000218; and Delta-like 4 has the Genbank accession number AF279305.

Among the Jagged sequences are human JAG1, Genbank accession number U61276.1. JAG1 has been reported to be expressed in cells adjacent to those expressing Notch2, suggesting a possible ligand receptor interaction. Human JAG2 has the Genbank accession number AF029778.1; and has been reported to interact with Notch 1.

Activators include derivatives, variants, and biologically active fragments of Delta and Serrate/Jagged polypeptides. A "variant" polypeptide means a biologically active polypeptide having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Fragments of interest may consist of the characteristic DSL domain necessary for Notch binding (see Shimizu et al. (2000) Biochem Biophys Res Commun. 276(1):385-9). Ordinarily, a biologically active variant will have an amino acid sequence having at least about 90% amino acid sequence identity with a native sequence polypeptide, preferably at least about 95%, more preferably at least about 99%.

A "chimeric" Delta and Serrate/Jagged polypeptide is a polypeptide comprising a polypeptide or portion (e.g., one or more domains) thereof fused or bonded to heterologous polypeptide. The chimeric polypeptide will generally share at least one biological property in common with a native sequence polypeptide. Examples of chimeric polypeptides include immunoadhesins, which combine a portion of the Delta/Serrate, or Jagged polypeptide with an immunoglobulin sequence, and epitope tagged polypeptides, which comprise a Delta/Serrate, or Jagged polypeptide or portion thereof fused to a "tag polypeptide". The tag polypeptide has enough residues to provide an epitope against which an antibody can be made, yet is short enough such that it does not interfere with biological activity of the Delta/Serrate, or Jagged polypeptide. Suitable tag polypeptides generally have at least six amino acid residues and usually between about 6-60 amino acid residues.

A "functional derivative" of a native sequence Delta/Serrate, or Jagged polypeptide is a compound having a qualitative biological property in common with a native sequence polypeptide. "Functional derivatives" include, but are not limited to, fragments of a native sequence and derivatives of a native sequence Delta/Serrate, or Jagged polypeptide and its fragments, provided that they have a biological activity in common with a corresponding native sequence polypeptide. The term "derivative" encompasses both amino acid sequence variants of Delta/Serrate, or Jagged polypeptides and covalent modifications thereof.

Other Notch activators of interest are binding partners specific for Notch extracellular domain, which bind to, and activate Notch. In one embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies that bind specifically to one of the Notch proteins are referred to as anti-Notch antibodies.

TGF-β blocking agents. A tissue regenerative agent of interest for use in the methods of the invention may block the TGF-β signaling pathway. As used herein, the terms "TGF-β" or "TGF-β gene product" or "TGF-β polypeptide" when used herein encompass native sequence TGF-β polypeptides, TGF-β polypeptide variants, TGF-β polypeptide fragments and chimeric TGF-β polypeptides. A "native sequence" polypeptide is one that has the same amino acid sequence as a TGF-β polypeptide derived from nature.

The term "native sequence TGF-β polypeptide" includes human TGF-β polypeptides. The TGF-β family of cytokines are ubiquitous, multifunctional and essential to survival. They play important roles in growth and development, inflammation and repair and host immunity. The mammalian TGF-β isoforms (TGF-β1, TGF-β2 and TGF-β3) are secreted as latent precursors and have multiple cell surface receptors of which at least two mediate signal transduction. TGF-β1, TGF-β2 and TGF-β3 all function through the same receptor signaling systems.

Members of the TGFβ superfamily are derived from inactive secreted precursor proteins through proteolytic processing. The precursors contain an N-terminal signal peptide, a central pro-domain containing 50-375 amino acids, and a C-terminal mature domain, which forms the active growth factor. The monomeric form of these growth factors contains 110-140 amino acids and has a compact structure with four antiparallel β strands and three intramolecular disulfide linkages forming a structure called a cystine knot. The cystine-knot domain is relatively resistant to denaturation. Much of the sequence variation among different TGFβ proteins is observed in the N-terminal regions, the loops joining the β strands, and the α helices. An additional N-terminal cysteine in each monomer links TGFβ monomers into functional homodimers and heterodimers.

Types I, II, and III TGFβ receptors are three different polypeptides with apparent molecular weights of 55, 85, and 280 kDa. The type I and type II receptors are both transmembrane serine/threonine kinases. Binding of TGFβ induces the formation of multimeric receptors, most likely heterotetramers, containing both the type I and type II receptors. The type II subunit then phosphorylates serine and threonine residues in a highly conserved sequence motif in the juxtamembrane region of the type I subunit, thereby activating its kinase activity. The type III TGFβ receptor is a cell-surface proteoglycan called β-glycan, which appears to regulate the accessibility of TGFβ to the signal-transducing heterotetramer of the type I and type II receptor. Residues near the C-terminus of R-Smad proteins are phosphorylated by activated type I TGFβ receptors. Phosphorylated R-Smads then dimerize with co-Smads. The resulting heterodimers translocate to the nucleus and cooperate with other transcription factors to activate transcription of specific target genes. Binding of different TGFβ-superfamily growth factors to their specific receptors elicits different cellular responses.

TGF-β blocking agents are agents that decrease TGF-β pathway signaling, for example through binding to the secreted TGF-β molecule and blocking the ability of TGF-β to interact with its receptors. Agents of interest may interact directly with TGF-β, e.g. antibodies, synthetic inhibitors, and the like, or may block downstream events. A number of TGF-β blocking agents have been described and are known in the art. For a review, see Yingling et al. (2004) Nature Reviews Drug Discovery 3:1011-1022, herein specifically incorporated by reference for teachings of antagonists, methods of use, and screening methods. Blocking agents may be specific for a TGF-β polypeptide, e.g. TGF-β1, 2 and/or 3; or may cross-react with one or more of the TGF-β polypeptides.

Known blocking agents includes include antibodies, which may be pan-neutralizing antibodies, isotype specific neutralizing antibodies, etc., and small molecule antagonists. TGF-β antagonists, including antibodies and antisense oligonucleotides, have been tested in clinical trials for various conditions. Several studies have shown the potential of targeting TGF-β signalling and neutralizing antibodies to TGF-β have been well tolerated. Large-molecule antagonists of TGF-β signalling, such as pan-neutralizing antibodies, TGF-β ligand isoform-specific antibodies and antisense molecules targeting TGF-β mRNA, are most advanced in clinical development, predominantly for fibrosis but with some therapies for cancer now beginning trials.

Small-molecule drug discovery efforts have mainly focused on the type I TGF-β receptor kinase, and most known TGF-β inhibitors have several common structural features, including a crucial 'warhead' group that contains a hydrogen-bond acceptor. Several companies have reported the efficacy of small-molecule inhibitors at inhibiting proliferative and immunosuppressive effects of TGF-β in cell-based assays and cancer models, and several candidates are in clinical trials.

Clinical trials have been reported by Muraoka et al. (2002) J Clin Invest. 109, 1551-9; Yang et al. (2002) J Clin Invest. 109, 1607-1615; Cordeiro et al. (1999) Invest Ophthalmol Vis Sci. 40, 2225-2234; Siriwardena et al. (2002) Ophthalmology. 109, 427-431; Cordeiro et al. (2003) Gene Ther. 10(1): 59-71). For example, a fully human monoclonal neutralizing antibody to TGF-β2 has been used in humans, including Phase III clinical trials. Second-generation antisense phosphorothiate oligonucleotides against TGF-β have also been tested in clinical trials. Examples of TGF-β antagonists are described by, for example, Peng et al. (2005) Biochemistry. 44(7):2293-304; Zhou et al. (2005) Arthritis Rheum. 52(1): 257-61; Phan et al. (2004) J Trauma 57(5):1032-7; U.S. Patent Application 20030125251; and U.S. Patent Application 20040038856.

Aged. As used herein, the term aged refers to the effects or the characteristics of increasing age, particularly with respect to the diminished ability of somatic tissues to regenerate in response to damage, disease, and normal use. One measure of aging, therefore, is evidenced by the inability of the organism to provide suitable signals for the activation of somatic stem cells. It is shown herein that such signals are soluble factors; and thus may be empirically measured, e.g. by functional assay such as the ability of soluble factors in the patient blood to induce stem cell activation in response to tissue damage; or by the ability to induce expression of Notch ligands, by binding assays such as ELISA, RIA; etc. with binding agents specific for Notch ligands; or by the ability to increase the levels of activated Notch, with Western analysis for activated, truncated Notch. etc.

Alternatively, aging may be defined in terms of general physiological characteristics. The rate of aging is very species specific, where a human may be aged at about 50 years; and a rodent at about 2 years. In general terms, a natural progressive decline in body systems starts in early adulthood, but it becomes most evident several decades later. One arbitrary way to define old age more precisely in humans is to say that it begins at conventional retirement age, around about 60, around about 65 years of age. Another definition sets parameters for aging coincident with the loss of reproductive ability, which is around about age 45, more usually around about 50 in humans, but will, however, vary with the individual.

Antibodies. In some embodiments of the invention, the tissue regenerative agent is an antibody. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, an antigen comprising an antigenic portion of the target polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the brain tumor protein target, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Antibodies with a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. Thus, humanized, chimeric, or xenogenic human antibodies, which produce less of an immune response when administered to humans, are preferred for use in the present invention.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by trypsin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif). Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879-5883 (1988) and Bird et al., Science 242:423-426 (1988), both fully incorporated herein, by reference. These are single chain Fvs which have been found to retain specificity and affinity and have been shown to be useful for imaging tumors and to make recombinant immunotoxins for tumor therapy. However, researchers have bound that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

Candidate antibodies can be tested for activity by a variety of methods. As a first screen, the antibodies may be tested for binding against the Notch protein of interest. After selective binding to the target is established, the candidate antibody may be tested for appropriate activity in an in vivo model, such as an appropriate cell line, or in an animal model. Antibodies may be assayed in functional formats, such as inducing stem cells to enter cell cycle; proliferation of stem cells, production of differentiated cells from stem cells; and the like, which may be assessed in culture or in an animal system.

Compound screening. Candidate modulators of Notch signaling or of TGF-β signaling may be identified by detecting the ability of an agent to affect the biological activity of the respective target. A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in binding.

Compounds of interest for screening include biologically active agents of numerous chemical classes, primarily organic molecules, although including in some instances inorganic molecules, organometallic molecules, genetic sequences, etc. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Compounds are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents may be assessed as described above for antibody screening, where an agent is tested for binding to Notch; and/or for an ability to activate the Notch pathway and induce a physiological response in stem cells.

Tissue Regeneration

The methods of the present invention utilize tissue regenerating agents as described above to enhance regeneration of tissues in aged animals. Such activity may be monitored by histological analysis, expression of genes indicative of stem cell activation; measurement of proliferation in stem cell compartments; and the like.

Analysis of proliferation may utilize staining for Ki67, which is a nuclear protein expressed in proliferating cells during late G1-, S-, M-, and G2-phases of the cell cycle, while cells in the G0 (quiescent) phase are negative.

One marker of certain stem cells is CD34, which is expressed, for example, by muscle satellite cells, hematopoietic stem cells, and many other organ stem cells. When these cells activate and differentiate into proliferative progenitor cells, CD34 is down-regulated. Another marker present on certain stem cells is CD133 (Yin et al. (1997) Blood 90(12):5002-12).

With the down-regulation of stem cell specific markers, differentiating cells will express tissue specific markers, which will vary depending on the type of stem cell being activated. For example, in muscle, the Pax-3 gene is expressed prior to differentiation of myogenic precursor cells into fusion-competent myoblasts, which fuse into myotubes, Pax-3 is then down-regulated, and other tissue specific markers expressed, e.g. Myf-5, desmin, eMHC, etc.

For screening purposes one may utilize in vitro assays for Notch or TGF-β biological activity, e.g. promoting proliferation and/or differentiation of stem cells, etc. Assays for biological activity of Notch may also include assays based on the processing pathway, including the cleavage of Notch, the release of the Notch intracellular domain, the translocation of Notch to the nucleus, and the expression of genes operatively linked to Hes/Hey promoters.

One screening assay of interest utilizes a hes or hey promoter operatively linked to a reporter gene; selectable marker, etc. The reporter construct is introduced into a cell line, particularly a cell line expressing a Notch protein of interest. The cell is then exposed to a candidate Notch activator. Activation of Notch is detected by expression of the hes/hey regulated gene. For example, a drug resistance marker may be operatively linked, where the cell requires Notch activation to grow in the presence of the drug. Alternatively, markers such as green fluorescent protein may be operatively regulated, where the fluorescent color is indicative of Notch activation. A hes reporter construct is described by Jarriault et al. (1998) Mol Cell Biol. 18(12):7423-31, herein specifically incorporated by reference. Other hes constructs are described, for example, by Wu et al. (2002) Mol Cell Biol. 22(21):7688-700; and Yan et al. (2002) Biochem Biophys Res Commun. 291(3):582-7.

Delivery of Tissue Regenerating Agent

The tissue regenerating agent(s) are incorporated into a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration can be achieved in various ways, usually by oral administration. The agent may be systemic after administration or may be localized by virtue of the formulation, or by the use of an implant that acts to retain the active dose at the site of implantation.

In pharmaceutical dosage forms, the tissue regenerating agent(s) and/or other compounds may be administered in the form of their pharmaceutically acceptable salts, or they may also be used alone or in appropriate association, as well as in combination with other pharmaceutically active compounds. The agents may be combined to provide a cocktail of activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Formulations are typically provided in a unit dosage form, where the term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Those of skill will readily appreciate that dose levels can vary as a function of the specific agent, the severity of the symptoms and the susceptibility of the subject to side effects. Some of the agents will be more potent than others. Preferred dosages for a given agent are readily determinable by those of skill in the art by a variety of means. A preferred means is to measure the physiological potency of a given compound.

Therapeutic Methods

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

For the treatment of disorders in which there is inadequate stem cell activation or there is a rapid deterioration of tissues due to an injury or disease, tissue regenerating agent(s) are administered at a dose that is effective to cause an increase of stem cell activation, but which maintains the overall health of the individual. Treatment regimens will often utilize a short-term administration of the active agent; although the treatment may be repeated as necessary. The treatment regime can require administration for prolonged periods, but may be administered as a single dose monthly, semi-monthly, etc. The size of the dose administered must be determined by a physician and will depend on a number of factors, such as the nature and gravity of the disease, the age and state of health of the patient and the patient's tolerance to the drug itself.

In a specific embodiment, the tissue regenerating agent(s) can be used for treatment of patients by means of a short-term administration, e.g. of 1, 2, 3 or more days, up to 1 or 2 weeks, in order to obtain a rapid, significant increase in activation.

For example, a number of conditions relevant to aged populations are characterized by an inability to regenerate tissues. All aged organs and tissues undergo a loss of regeneration and maintenance with age, thus this method is applicable to the aged organ systems in general, including muscle, brain, blood, bones, liver, etc.

Examples of muscular disorders which may be treated include skeletal muscle diseases and disorders; cardiac muscle pathologies; smooth muscle diseases and disorders, etc., particularly Duschenne Muscular Dystrophy, cardiomyopathy, atherosclerosis.

Stem Cell

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Stem cells of interest include muscle satellite cells; hematopoietic stem cells and progenitor cells derived therefrom (U.S. Pat. No. 5,061,620); neural stem cells (see Morrison et al. (1999) Cell 96:737-749); embryonic stem cells; mesenchymal stem cells; mesodermal stem cells; liver stem cells, etc.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

Tissues

One tissue of interest for the present invention is muscle. The term muscle cell as used herein refers to any cell that contributes to muscle tissue. Myoblasts, satellite cells, myotubes, and myofibril tissues are all included in the term "muscle cells". Muscle cell effects may be induced within skeletal, cardiac and smooth muscles, particularly with skeletal muscle.

Activation of satellite cells in muscle tissue can result in the production of new muscle cells in the patient. Muscle regeneration as used herein refers to the process by which new muscle fibers form from muscle stem cells. A useful Notch activating agent will usually confer an increase in the number of new fibers by at least 1%, more preferably by at least 20%, and most preferably by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter; etc. An increase in growth of a muscle fiber can be defined as an increase in the diameter where the diameter is defined as the minor axis of ellipsis of the cross section.

Muscle regeneration may also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average S time required for the number of cells in the culture to increase by a factor of two. A useful therapy may increase satellite cell activation relative to a control, by at least 10%, more preferably by at least 50%, and most preferably by more than 100%, for example as assessed by mitotic index. Alternatively, satellite cell activation in vivo may be detected by monitoring the appearance of the intermediate filament vimentin by immunological or RNA analysis methods. When vimentin is assayed, a useful activator may cause expression of detectable levels of vimentin in the muscle tissue when the therapeutically useful dosage is provided. Productive muscle regeneration may be also monitored by an increase in muscle strength and agility.

Muscle regeneration may also be measured by quantitation of myogenesis, i.e. fusion of myoblasts to yield myotubes. An effect on myogenesis results in an increase in the fusion of myoblasts and the enablement of the muscle differentiation program. For example, the myogenesis may be measured by the fraction of nuclei present in multinucleated cells in relative to the total number of nuclei present. Myogenesis may also be determined by assaying the number of nuclei per area in myotubes or by measurement of the levels of muscle specific protein by Western analysis.

The survival of muscle fibers may refer to the prevention of loss of muscle fibers as evidenced by necrosis or apoptosis or the prevention of other mechanisms of muscle fiber loss. Muscles can be lost from injury, atrophy, and the like, where atrophy of muscle refers to a significant loss in muscle fiber girth.

In addition to skeletal muscle formation, the regeneration of cardiac muscle in the aging is of interest. For example, following an event such as myocardial infarction; surgery, catheter insertion, atherosclerosis, and the like, cardiac muscle can be damaged. Such damage is not easily repaired in elderly patients, resulting in a loss of function. Administration of Notch activating agents following such incidents of muscle damage can increase regeneration of the damaged tissues. The agents may be administered systemically, or using a stent, catheter, implant, and the like that increase the local concentration of the active agent.

Hematopoietic stem cells (HSCs) have the ability to renew themselves and to give rise to all lineages of the blood. Conditions of the aged that benefit from activation of HSC include, for example, conditions of blood loss, such as surgery, injury, and the like, where there is a need to increase the number of circulating hematopoietic cells. Anemia is an abnormal reduction in red blood cells, which can occur from a malfunction in the production of red blood cells. Weakness and fatigue are the most common symptoms of even mild anemia. Anemia in the elderly is often due to causes other than diet, particularly gastrointestinal bleeding or blood loss during surgery. Anemia in older people is also often due to chronic diseases and folic acid and other vitamin deficiencies.

In conditions of the aged where there is a requirement for hematopoietic cell generation, a formulation of Notch activating agent is administered, e.g. following incidents that incur blood loss, and the like.

Neural stem cells are primarily found in the hippocampus, and may give rise to neurons involved in cognitive function, memory, and the like. Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny.

Aged individuals often suffer from a diminution of neural function. As such, these cells find use in the treatment of a variety of conditions, including traumatic injury to the spinal cord, brain, and peripheral nervous system; treatment of degenerative disorders including Alzheimer's disease, Huntington's disease, Parkinson's disease; stroke; and the like.

Alzheimer's disease accounts for half to two thirds of all dementia cases. Other causes of dementia include vascular disease (atherosclerosis of the brain blood vessels); traumatic brain injury; Parkinson's, Huntington's, Creutzfeldt-Jakob, and other diseases. Alzheimer's disease is uncommon below 65 years, occurring in fewer than 5% of people aged 65-70, and then increasing in frequency rapidly, so that by 95 years of age as many as 55% of people are affected.

Older adults are also at risk for neural damage resulting from stroke. Older age is also linked with higher rates of post-stroke dementia. Stroke occurs as a result of blood flow blockage to the brain. A reduction of, or disruption in, blood flow to the brain is the primary cause of a stroke. Blockage for even a short period of time can be disastrous and cause brain damage or even death. Ischemic strokes are the more common type, causing over 80% of all strokes.

Parkinson's disease (PD) is a slowly progressive disorder that affects movement, muscle control, and balance. Most Parkinson's victims are elderly. PD develops as cells are destroyed in certain parts of the brain stem, particularly the crescent-shaped cell mass known as the substantia nigra. Nerve cells in the substantia nigra send out fibers to the corpus stratia, gray and white bands of tissue located in both sides of the brain. There the cells release dopamine, an essential neurotransmitter (a chemical messenger in the brain). Loss of dopamine in the corpus stratia is the primary defect in Parkinson's disease.

Stem cells may also be present in the epidermis, giving rise both to epidermal and mesenchymal tissues. Like all the body's tissues, the skin undergoes many changes in the course of the normal aging process. The cells divide more slowly, and the inner layer of the dermis starts to thin. Fat cells beneath the dermis begin to atrophy. In addition, the ability of the skin to repair itself diminishes with age, so wounds are slower to heal. The thinning skin becomes vulnerable to injuries and damage. The underlying network of elastin and collagen fibers, which provides scaffolding for the surface skin layers, loosens and unravels. Skin then loses its elasticity. When pressed, it no longer springs back to its initial position but instead sags and forms furrows. The skin is more fragile and may bruise or tear easily and take longer to heal.

In response to damage of aged skin, for cosmetic purposes, following trauma such as burns, abrasions, etc., it is beneficial to stimulate activation of stem cells. Activating agents may be administered topically, e.g. in combination with agents to enhance penetration through the dermal layers, systemically, using implants, etc.

In many clinical situations, the bone healing condition are less ideal due to decreased activity of bone forming cells, e.g. within aged people. Within bone marrow stroma there exists a subset of nonhematopoiethic cells capable of giving rise to multiple cell lineages. These cells termed as mesenchymal stem cells (MSC) have potential to differentiate to lineages of mesenchymal tissues including bone, cartilage, fat, tendon, muscle, and marrow stroma.

A variety of bone and cartilage disorders affect aged individuals. Such tissues are normally regenerated by mesenchymal stem cells. Included in such conditions is osteoarthritis. Osteoarthritis occurs in the joints of the body as an expression of "wear-and-tear". Thus athletes or overweight individuals develop osteoarthritis in large joints (knees, shoulders, hips) due to loss or damage of cartilage. This hard, smooth cushion that covers the bony joint surfaces is composed primarily of collagen, the structural protein in the body, which forms a mesh to give support and flexibility to the joint. When cartilage is damaged and lost, the bone surfaces undergo abnormal changes. There is some inflammation, but not as much as is seen with other types of arthritis. Nevertheless, osteoarthritis is responsible for considerable pain and disability in older persons.

In conditions of the aged where repair of mesenchymal tissues is decreased, or there is a large injury to mesenchymal tissues, the stem cell activity may be enhanced by administration of tissue regenerating agent(s).

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

A hallmark of aging is diminished regenerative potential of tissues, but the mechanism of this decline is unknown. Analysis of injured muscle revealed that, with age, resident precursor cells (satellite cells) had a markedly impaired propensity to proliferate and to produce myoblasts necessary for muscle regeneration. This was due to insufficient up-regulation of the Notch ligand Delta and, thus, diminished activation of Notch in aged, regenerating muscle. Inhibition of Notch impaired regeneration of young muscle, whereas forced activation of Notch restored regenerative potential to old muscle. Thus, Notch signaling is a key determinant of muscle regenerative potential that declines with age.

Quiescent skeletal muscle precursor cells, or satellite cells, are positioned between the basal lamina and the plasma membrane of muscle fibers. In response to injury, these cells undergo activation, a process defined as the break from quiescence and the initiation of cell proliferation. They then progress along a myogenic lineage pathway to generate myoblasts, which ultimately fuse to each other or to injured myofibers to promote repair and regeneration. Satellite cells represent the endogenous source of muscle precursor cells and account for more than 99% of the regenerative potential of adult muscle. The efficacy of skeletal muscle regeneration is markedly impaired with age, but the role of age-related changes in satellite cell activation in this decline is unknown.

We recently showed that satellite cell activation, proliferation, and differentiation commitment are regulated by the Notch signaling pathway, a pathway well characterized for its role in myogenesis and in tissue formation during embryogenesis. Although alterations in Notch signaling have been associated with developmental abnormalities and diseases, changes in Notch signaling have not been implicated in the aging process. These studies demonstrate that the age-related decline of muscle regenerative potential is due to a decline in Notch signaling and can be reversed by Notch activation.

Figure 5:
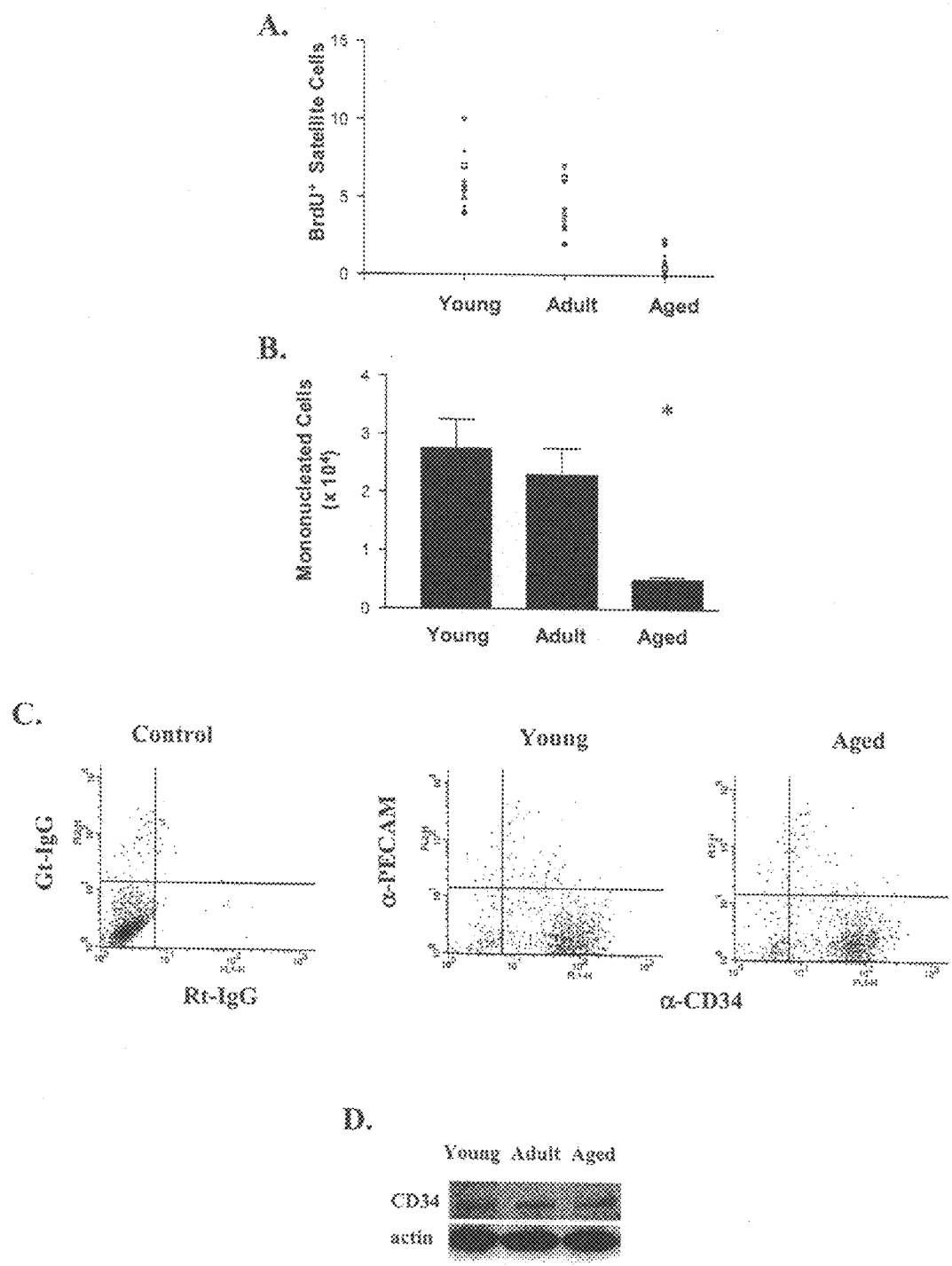
FIG. 5A-5D. Two days following muscle injury in vivo, and 2 hrs after BrdU injections, bulk myofiber explants were prepared and analyzed for the number of BrdU$^+$ cells associated with myofiber fragments (FIG. 1A). This figure shows a scatter plot, each point representing the quantitation of the analysis of an individual microscopic field from preparations from 3 individual mice at each age. The means and standard deviations from young, adult, and aged preparations were 6.0±2.0, 4.2±1.7, and 1.2±0.6, respectively. B. Bulk myofiber explants were prepared, and the cultures were allowed to expand in vitro (see FIG. 1B). Individual cultures from 4 young, adult, and aged mice were prepared, and the total number of cells produced after 4 days are presented graphically as means±S.D (*p<0.001 compared to young or adult). For the young cultures, approximately 80% of the cells were M-cadherin⁺ and approximately 50% of the cells were desmin⁺ at this time point. The percentage of desmin⁺ cells in old cultures at this time point (see FIG. 1B) was approximately 20% because of the limited proliferation of myogenic cells but the still rapid proliferation of non-myogenic cells. C. Purified satellite cells isolated from resting muscle (as in FIG. 1C) were co-stained with antibodies specific for cell surface molecules PECAM and CD34 and analyzed by FACS. Goat IgG and Rat IgG were used as isotype-matched negative controls. Triplicate experiments produced similar results. D. Myofiber explant cultures isolated from skeletal muscle of different age were used to prepare protein extracts and immunoblot analysis was performed with anti-CD34 and anti-actin antibodies. No significant difference in the levels of CD34 expression was observed between these ages.

The diminished regenerative potential of aged muscle was evident when injured hindlimb muscles of young (2 to 3 months), adult (5 to 7 months), and aged (23 to 24 months) mice were analyzed for activated, proliferating satellite cells associated with the myofibers (FIG. 1A; FIG. 5). Accordingly, many fewer myoblasts were generated in myofiber explant cultures from aged mice than from young or adult mice (FIG. 5B). This difference was dramatically apparent when the cells were induced to differentiate, even though there was no major defect in the propensity of aged myoblasts to fuse (FIG. 1B). This age-related decline in myoblast generation is consistent with results from single fiber preparations.

Figure 2:
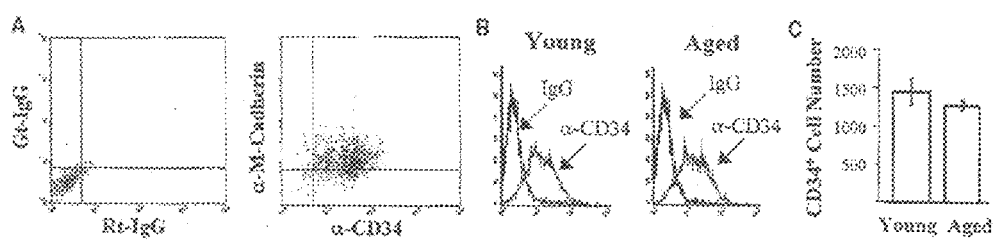
FIG. 2A-2C. Satellite cell numbers from mice of different ages. (A). Purified populations of satellite cells were derived from adult muscle. Cells were costained with antibodies to CD34 and M-cadherin and subjected to flow cytometry. (Left) Negative controls; (right) more than 95% of cells were CD34$^+$/M-cadherin$^+$. Similar results were obtained from muscles of all ages (n≧5). (B) Satellite cells were purified from young and aged muscles, stained with a CD34-specific or control antibody, and analyzed by FACS. The analysis shows cell count on the y axis and the immunofluorescence of either the control (IgG) or CD34-specific antibody on the x axis. (C) The numbers of CD34$^+$ satellite cells from young and aged skeletal muscle were determined in multiple independent experiments. Data represent means±S.D (n=4).

Previous studies, using various methodologies to study different muscles from different species, have diverged in their conclusions as to whether there is a decline, no change, or even a relative increase in satellite cell density with age. To determine whether a decrease in satellite cell number with age might account for the diminished myoblast production that we observed, we quantified purified satellite cells isolated from mouse hindlimb muscles over this age range. Fluorescence-activated cell sorting (FACS) analysis demonstrated that nearly 100% of the purified cells expressed both CD34 and M-cadherin (FIG. 2A), and less than 2% of the cells expressed the endothelial cell marker PECAM (FIG. 5C), which confirmed that these were indeed satellite cells. There was no significant difference in satellite cell number between young and old muscle (FIG. 2, B and C). This was confirmed by Western blot analysis of CD34 expression in myofiber explants (FIG. 5D). Therefore, the dramatic age-related decline in myoblast generation in response to injury is due to an impairment of activation rather than a decline in number of satellite cells.

Figure 6:
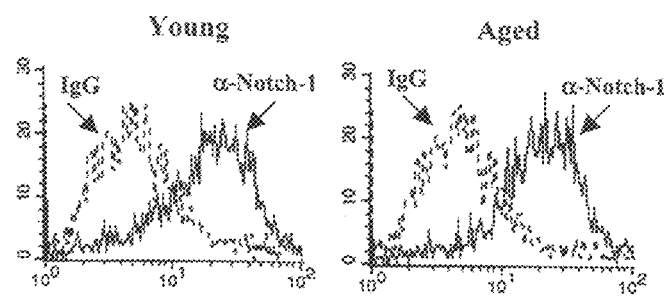
FIG. 6A-6D. Satellite cells isolated from young or old muscle were stained with an antibody specific to the extracellular domain of Notch-1 (8G10) and analyzed by FACS. The expression of full-length Notch-1 was the same in old satellite cells as in young cells. B. Satellite cells isolated from resting muscle of young mice or 1 day after a multifocal needle injury were co-stained with antibodies specific for Delta and for PCNA and analyzed by FACS. Rabbit IgG and mouse IgG were used as isotype-matched negative controls. Triplicate experiments produced similar results. C. Myofiber explant cultures with associated satellite cells were derived from mice of different ages (Young: "Y", Adult: "Ad", or Aged: "Ag"). Either at time 0 or 24 hrs after explantation, cultures were used for Western analysis with antibodies specific for Delta and actin. Unlike young and adult cells, aged fibers and associated satellite cells failed to up-regulate Delta in response to muscle injury induced by explantation. Similar results were obtained in 3 independent experiments. As shown previously, primary myoblast cultures (Mb) express high levels of Delta. D. Explant cultures were analyzed for components of the Notch signaling pathway by immunoblot analysis at different times after explantation. An antibody against the C-terminal of Notch identifies both the inactive form ("TM"—transmembrane) and the cleaved, active form ("Notch-1*"). Actin was used as a loading control. Similar results were obtained in 3 independent experiments.
Figure 6:
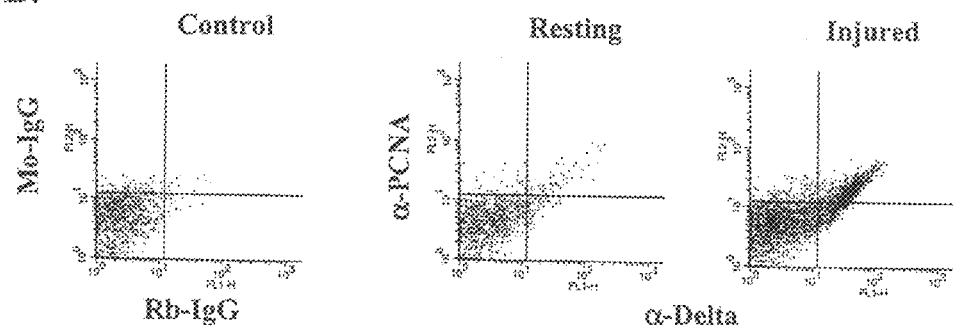
Figure 6:
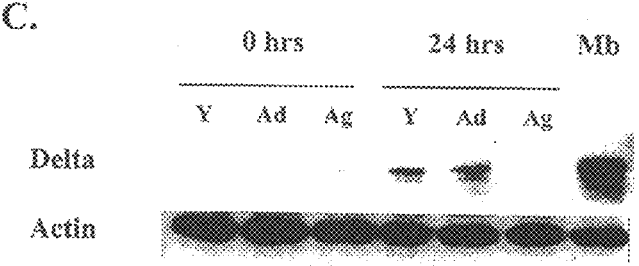
Figure 6:
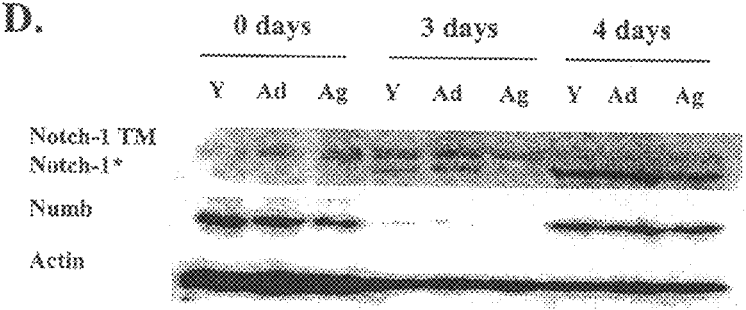

Because Notch signaling plays a critical role in satellite cell activation and adult muscle regeneration, we compared satellite cells from adult and aged muscle for the expression of Notch-1, its ligand Delta-1, and its inhibitor Numb. In satellite cells from resting muscle of all ages, there was negligible expression of Delta-1 and high levels of Numb expression (FIG. 3A; FIG. 6, B and C), consistent with previous results, and the levels of full-length Notch-1 were very similar (FIG. 6A).

Figure 3:
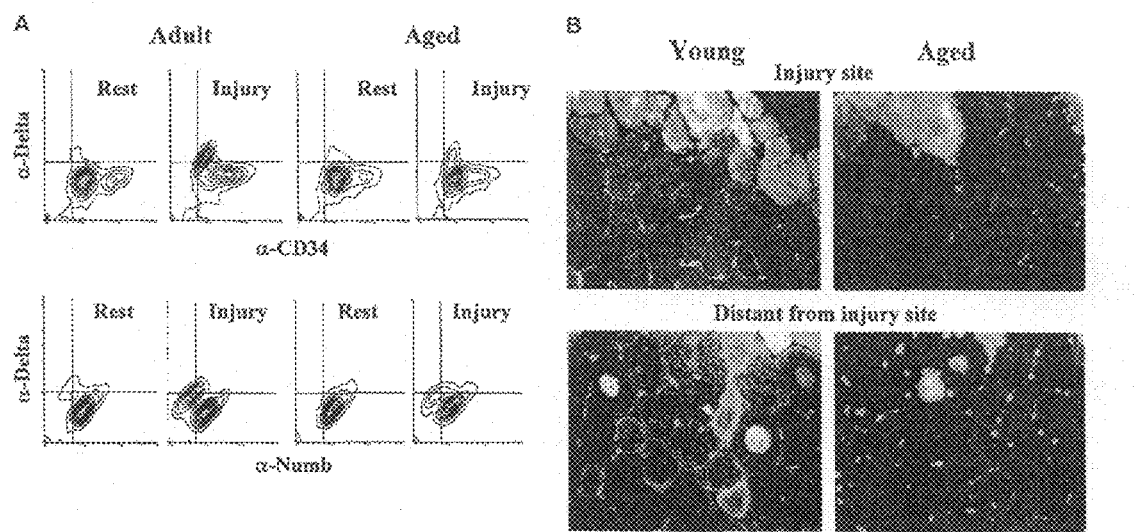
FIG. 3A-3B. The regulation of Delta expression in satellite cells and in muscle tissue during muscle regeneration. (A) Delta up-regulation in satellite cells in response to injury. (Top) Satellite cells were purified from muscle of mice of different ages, either before injury (rest) or 1 day after injury; costained with antibodies to CD34 and Delta; and analyzed by FACS. Injury induced the expression of Delta in a large percentage (~35%) of the cells from adult muscle but in a small percentage (~7%) of cells from aged muscle (n=4). (Bottom) Satellite cells were also analyzed for the simultaneous expression of Delta and Numb at rest or in response to injury and revealed a coordinate increase in Delta and decrease in Numb in activated satellite cells from young or adult muscle. Similar results were obtained in three independent experiments. (B) Muscles from young and aged mice were subjected to freeze injury. The mice were injected with Evans blue dye 12 hours later and killed after 24 hours. Muscle cryosections were analyzed by immunofluorescence using a Delta-specific antibody (green) and Hoechst dye (blue). Evans blue dye, which is taken up only by injured fibers, appears red. Two cross-sectional areas are shown for each age. The top panels are through the injury site at the border of the injury. The bottom panels are cross sections ~300 μm caudal to the injuries. Results were similar in four independent experiments. Delta expression in adult muscle was similar to that shown for young muscle (and see FIG. 6C).

In response to injury, satellite cells from young and adult muscle up-regulated Delta-1, whereas old satellite cells failed to do so (FIG. 3A; FIG. 6C). Delta up-regulation was associated with cell proliferation as demonstrated by PCNA staining (FIG. 6B). Interestingly, increased Delta expression was associated with decreased Numb expression (FIG. 3A). Analysis of multiple experiments demonstrated that there were about one-fourth as many activated satellite cells (CD34$^+$/M-cad$^+$/Delta$^+$/Numb$^-$) in old muscle as in young or adult muscle in response to injury.

We used immunoblot analysis to test whether the reduced Delta up-regulation after injury was associated with lower levels of activated Notch in old cells. The levels of transmembrane Notch-1 were similar in cultures of all ages (FIG. 6D). However, there were consistently lower levels of activated Notch in old satellite cells activated ex vivo. The biphasic pattern of Numb expression during activation of aged satellite cells was similar to that previously described in young cells. We also analyzed the expression of Delta after muscle injury in vivo in young and aged mice. In young mice, Delta was induced adjacent to the injury site not only in satellite cells, but also prominently at myofiber membranes and possibly in interstitial cells in this region (FIG. 3B). This pattern was also observed at a distance from the injury site, which suggested a diffusible signal for Delta up-regulation. By contrast, there was almost no up-regulation of Delta in old muscle after injury, a finding confirmed by Western analysis, which included both satellite cells and myofibers (FIG. 6C).

Figure 7:
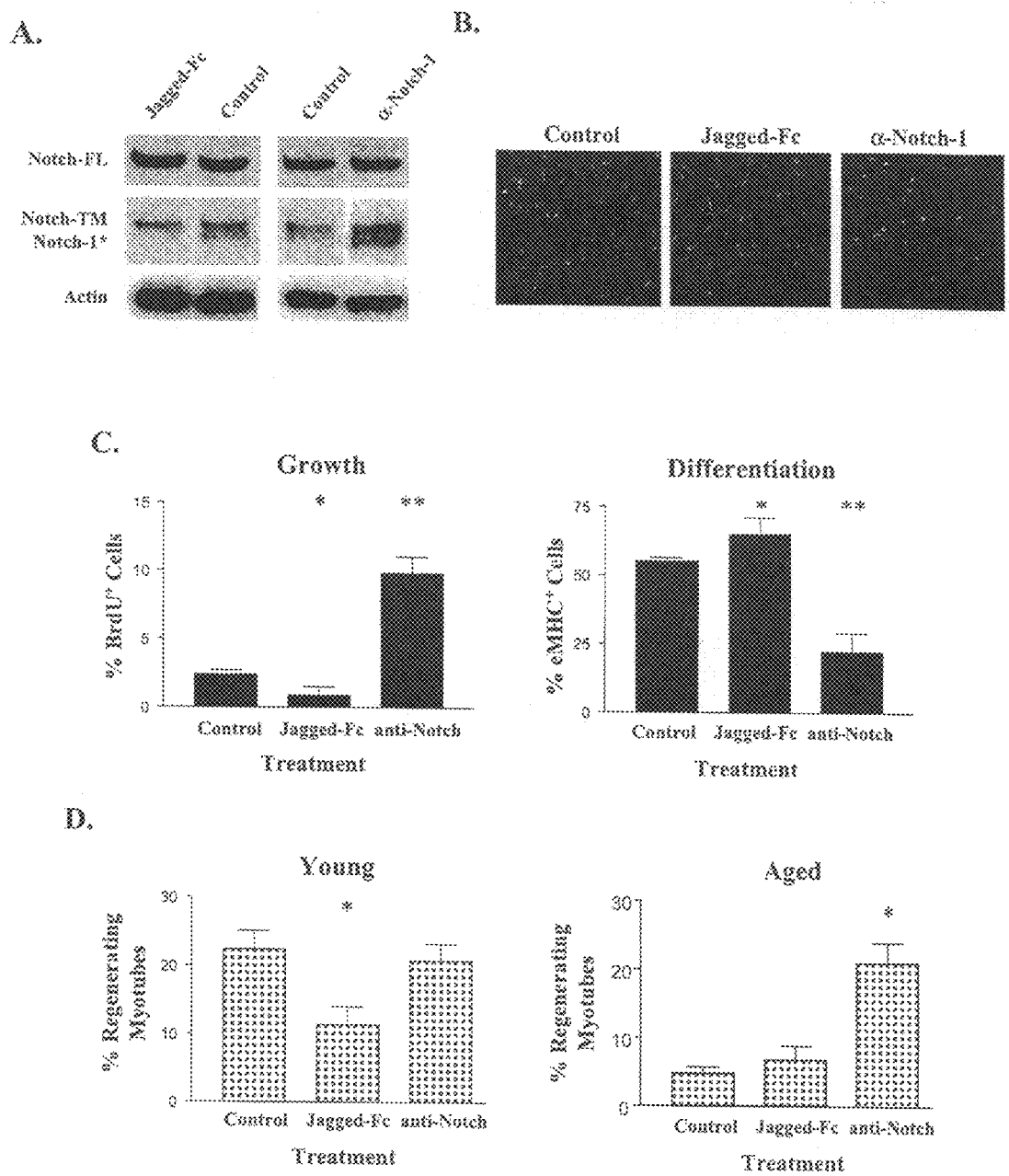
FIG. 7A-7D. Myoblasts from explants were incubated with Jagged-Fc complexed with anti-Fc or with anti-Fc alone (control). Alternatively, cells were plated on dishes coated with immobilized anti-Notch-1 antibody (8G10) (-Notch-1") or control antibody ("control") for 24 hrs. The cultures were then analyzed by immunoblot analysis for full-length ("FL"), transmembrane ("TM"), and active ("Notch-1*") Notch. Actin was used as a loading control. (n=3). B. Myoblasts were treated in culture with control protein complexes, with Jagged-Fc, or with anti-Notch-1 as described above and maintained in differentiation medium for one day. The cultures were labeled with BrdU for the last 2 hours and then analyzed for BrdU incorporation using an anti-BrdU antibody (green) and for differentiation using an antibody against embryonic myosin heavy chain (eMHC) (red). Hoechst dye (blue) was used to label all nuclei. C. From multiple experiments as shown in panel (B), the effects of treatment with Jagged-Fc and αNotch-1 were quantitated (n=3 or 4 for each condition). Jagged-Fc inhibited proliferation (decreasing BrdU incorporation from 2.4±0.3 for control to 0.9±0.6; *p<0.05) and enhanced differentiation (increasing the percentage of cells expressing eMHC from 55.1±1.3 for controls to 65.1±5.9; *p<0.05). Treatment with the αNotch-1 antibody had the opposite effects, inducing proliferation (increasing BrdU incorporation from 2.4±0.3 for control to 9.8±1.2; p<0.001) and inhibiting differentiation (decreasing the percentage of cells expressing eMHC from 55.1±1.3 for controls to 22.3±6.7; p<0.001) of these cells even in the low serum conditions. D. Effects of Jagged-Fc and αNotch-1 antibody on muscle regeneration in vivo. From multiple experiments shown representatively in FIG. 2C, we analyzed H&E-stained sections for the number of central nucleated, regenerating myotubes in the field of injury under each condition. Total numbers of myotubes were counted for each injury site (3 mice for each treatment at each age; n≧7 injury sites for each condition; *p<0.005 compared to controls). Jagged-Fc markedly inhibited regeneration of young muscle, and α-Notch-1 antibody significantly enhanced regeneration of old muscle. Notably, activation of Notch signaling did not further enhance regeneration of young muscle, which was already optimal, and inhibition of Notch signaling did not further inhibit the regeneration of aged muscle, which was already markedly impaired compared to young muscle.

To further test the significance of Notch signaling for regeneration of young and aged muscle, we introduced specific inhibitors and activators of Notch at sites of injury and analyzed their effects on muscle repair. To inhibit Notch activation we used a soluble Jagged-Fc fusion protein, which in vitro blocked Notch activation, decreased cell proliferation, and enhanced differentiation of myogenic cells (FIG. 7, A to C). When Jagged-Fc was introduced at sites of injury, there was a marked inhibition of young muscle regeneration (FIG. 4).

Figure 4:
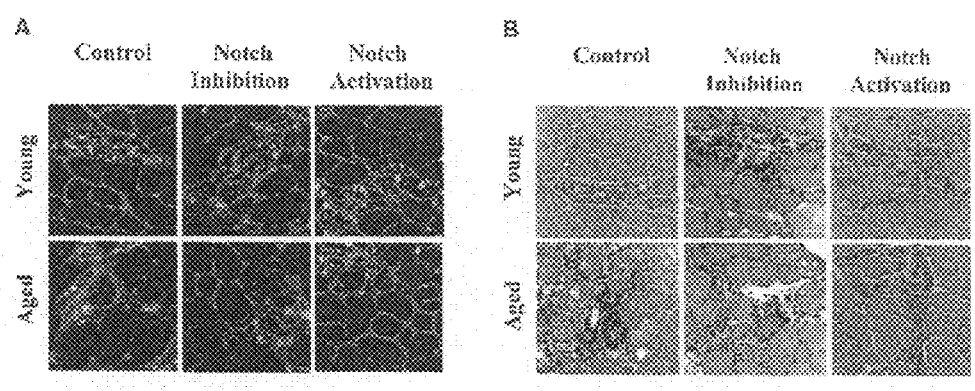
FIG. 4A-4B. Experimental modulation of Notch signaling dramatically affects muscle regeneration in young and aged muscle. (A) Muscles of young or aged mice were injected with an inhibitor of Notch signaling (Jagged-Fc), an activator of Notch signaling (Notch-1 specific antibody), or respective controls (see FIG. 7, A to C). Two days later, BrdU was injected intraperitoneally. Muscles were removed 5 days after injury. Immunofluorescence was performed on sections using antibodies to BrdU (green) and laminin (red). Laminin staining delineates boundaries of nascent and mature myofibers. The inhibition of Notch by Jagged-Fc reduced BrdU incorporation into nascent myotubes and reduced myotube formation in young muscle, whereas activation of Notch by antibody against Notch-1 promoted BrdU incorporation and regeneration in old muscle. (B) Hematoxylin and eosin staining confirms the dramatic inhibitory effect of Jagged-Fc on regeneration of young muscle and the dramatic positive effect of Notch-1 specific antibody on regeneration of old muscle. At least three mice of each age were used for the quantitative analysis for each condition (FIG. 7D).

Whereas regenerating young muscle was essentially devoid of inflammatory cells and nascent scar formation, the presence of the Notch inhibitor led to ineffective regeneration, similar to that seen in old muscle (FIG. 4). Analysis of multiple experiments showed a dramatic and consistent reduction in the number of regenerating myotubes in young muscle treated with Jagged-Fc compared with control treatment (FIG. 7D).

We then tested whether forced activation of Notch could improve regeneration of aged muscle. We activated Notch directly, using an antibody to its extracellular domain (FIG. 7A), which resulted in an increase in cell proliferation and an inhibition of myogenic differentiation in vitro (FIG. 7, B and C). Strikingly, acute activation of Notch signaling in vivo markedly improved the regeneration of old muscle, rendering it similar to young muscle (FIG. 4, A and B). Analysis of multiple experiments showed that Notch activation at the time of injury reproducibly and significantly enhanced the formation of regenerating myotubes in aged, injured muscle (FIG. 7D). Therefore, Notch activation is not only necessary for regeneration of young muscle but also sufficient to promote effective regeneration of aged muscle.

The results of this study demonstrate that inadequate activation of Notch-1 by Delta contributes to the loss of regenerative potential in old skeletal muscle. We propose that a decline in Notch signaling necessary for cell proliferation and cell fate determination may also occur in progenitor cells and stem cells in other tissues with age and may be a general mechanism underlying the diminished regenerative properties of aged tissues.

Materials and Methods

Reagents. Antibodies to Delta, M-cadherin, PECAM, and PCNA were purchased from Santa Cruz Biotechnology (Santa Cruz, Calif.), to CD34 and Numb from Beckton-Dickinson (San Jose, Calif.), to actin and laminin from Sigma (St. Louis, Mo.), and to Notch-1 from Upstate Biotechnology (Lake Placid, N.Y.). The anti-BrdU staining kit was purchased from Beckton-Dickinson. Fluorophore-conjugated secondary antibodies for flow cytometry and immunofluorescence were obtained from Caltag (Burlingame, Calif.) and used as previously described. Bromodeoxyuridine labeling reagent was from Zymed (South San Francisco, Calif.).

Mice. C57BL/6 male mice (2-24 mos old) were obtained from pathogen-free breeding colonies at Jackson Laboratories (Bar Harbor, Me.). Some of the aged mice were purchased from the NIA. All animals were maintained in the Veterinary Medical Unit of the VA Palo Alto Health Care System and handled in accordance with guidelines of the Administrative Panel on Laboratory Animal Care of Stanford University.

Muscle injury. Satellite cell activation. In order to induce activation of satellite cells for analysis of in vivo activation either associated with myofibers or by flow cytometry, hindlimb muscles were pierced multiple times with a 23-gauge needle. For each muscle (tibialis anterior, gastrocnemius, and quadriceps), the injury was distributed evenly and systematically to achieve uniform regenerative responses.

Tissue response to injury. In order to analyze biochemical changes in situ in response to injury, a small focal injury was made by an application of dry ice for 5 seconds directly to the tibialis anterior muscle. This produces a very reproducible "wedge" injury in the muscle with a discrete border between uninjured and injured muscle, and this border remains clear and distinct during the regeneration of the injured tissue.

Analysis of regeneration in response to changes in Notch signaling. For studies of muscle regeneration in the presence of regulators of Notch signaling, single needle-track injuries were used for analyses (see below). The needle is inserted at an angle of approximately 450 with respect to the longitudinal axis of the fibers. This produces an injury that is approximately 2-4 fiber diameters across in the dimension that reflects the width of the needle, and approximately 5-10 fibers "long", representing the passage of the needle obliquely throughout the section. Thus, on average, approximately 20 damaged fibers are apparent in a cross section through the needle track, and approximately 20 regenerating myotubes are seen beginning around 3-4 days after the injury and growing over the next two weeks in young, healthy muscle.

Bulk myofiber explant cultures. Hindlimb muscles were isolated from young, adult and old mice and preparation of myofiber fragments were obtained by collagenase type II digestion, trituration, and multiple sedimentation and washing procedures as previously described. Confocal microscopic analysis confirmed that the vast majority of nuclei were located underneath the myofibers' basal laminae (as determined by staining with an anti-laminin antibody) and thus were either satellite cell nuclei or myonuclei, and that most interstitial cells had been eliminated from the preparation. Based on this microscopic analysis, we estimate that fewer than 5% of the mononucleated cells are not satellite cells at time 0. With time in culture, the percentage of the non-myogenic cells increases compared to myogenic cells because of an apparently greater proliferation rate, particularly in aged cultures because of the limited activation and proliferation of myofiber-associated satellite cells.

For studies of satellite cell activation ex vivo, bulk myofiber explants were resuspended in growth medium consisting of Ham's F-10 nutrient mixture (Mediatech, Herndon, Va.) with 20% fetal bovine serum (FBS) (Mediatech), 5 ng/ml basic fibroblast growth factor (Atlanta Biological, Atlanta, Ga.), and 1% penicillin/streptomycin (pen/strep) (Invitrogen, Carlsbad, Calif.) and cultured in 6-well plates coated with 5 µg/ml laminin (Invitrogen) and 0.002% collagen (Sigma) at 37° C. in 5% $CO_2$. Differentiation medium consisted either of OptiMem (Invitrogen) supplemented with 1% FBS and pen/strep, or of Dulbecco's modified Eagle's medium (Mediatech) supplemented with 2% horse serum (Mediatech).

Satellite cell isolation. For the purification of satellite cells, muscles of equivalent wet weights from mice of different ages were subjected to the same procedure described above for bulk myofiber explants. Satellite cells were then isolated by a second purification step, beginning with extensive washing with PBS to remove loosely adherent cells but retaining satellite cells, which are situated beneath the basal lamina. The satellite cells were then liberated by further digesting the myofiber fragments in 10 volumes of phosphate buffered saline (PBS), 0.5 U/ml dispase (Invitrogen), 38 U/ml collagenase type II (US Biological, Swampscott, Mass.) for 30 minutes at 37° C. with agitation. FBS (1:10 by volume) was added to digests which were then subjected to centrifugation at 500 g 1 minute to pellet fiber debris, filtration through 50 micron mesh, and centrifugation at 1,000 g for 5 minutes to pellet satellite cells. The resulting preparation contained mononucleated cells that were almost all satellite cells (see FIG. 1C) and could be distinguished from remaining debris on FACS analysis by the characteristic forward scatter and side scatter properties of the cells.

Immunofluorescence. Muscles were dissected and embedded for cryostat sectioning as previously described. Tissue sections were washed in staining buffer (1% FBS in PBS) and blocked for 30 min in staining buffer containing 0.25% Triton X-100. Primary and isotype-matched control antibodies were diluted in staining buffer (1 µg/100 µl). Sections were stained for 2 hours at room temperature, washed in staining buffer, and incubated with fluorochrome-conjugated secondary antibodies, diluted 1:500 in staining buffer with Hoechst dye, for 1 hour at room temperature. Cells in culture were fixed in 6-well plates for immunofluorescence analysis, and all procedures were as previously described.

Fluorescent activated cell sorting (FACS). Cells were fixed with 4% paraformaldehyde. For the analysis of intracellular epitopes, cells were permeabilized with staining buffer containing 0.1% Triton-X 100. Cells were then stained with primary antibodies or with isotype-matched control antibodies (1 µg in 100 µl) for 1 hour at room temperature, followed by incubation with fluorochrome-labeled secondary antibodies (1:200-1:500 dilutions) for 45 min at room temperature. $4 \times 10^3 - 10^4$ cell events were collected in each assay. Cells were analyzed by FACScan (Beckton-Dickinson), using compensation for green and red fluorescence and doublet discrimination parameters. As noted above, for purified satellite cell preparations, cells were distinguished from non-cellular debris by the forward and side scatter gating.

Western Blotting. For Western analysis, cells and myofiber explants were detached and lysed in RIPA buffer (50 mM Tris-HCl, 1 mM EDTA, 1 mM EGTA, 150 mM NaCl, 1% NP-40) containing 90 µg/ml PMSF, 20 µg/ml aprotinin and 20 µg/ml leupeptin (Sigma). Immunoblotting was performed as previously described.

Jagged-1Fc and anti-Notch-1 antibody treatment. Jagged-1 Fc (10 µg; R&D systems, Minneapolis, Minn.) was incubated for 1 hour on ice with anti-human Fc antibody (5 µg; Sigma) to give a 2:1 stoichiometric ratio and a final concentration of Jagged-Fc of 100 µg/ml. The $ED_{50}$ for inhibiting Notch-dependent C2C12 cell proliferation is typically 2-10 µg/ml according to the manufacturer. The Jagged-Fc/anti-Fc complex, or the anti-Fc antibody alone, was incubated with $5 \times 10^5$ cells at room temperature for 30 minutes, after which cells were cultured as usual. Jagged-Fc alone (not complexed to with the anti-Fc antibody) was also tested and found to be effective in inhibiting Notch signaling. For anti-Notch antibody treatment, laminin/collagen coated plates were further coated with a mixture containing 10 µl anti-Notch antibody supernatant (hybridoma clone 8G10, Upstate Biotechnology) or an isotype-matched hamster IgG and 2.5

µg of either goat IgG or gamma globulin in 1 ml PBS at 4° C. overnight. Cells were cultured on these coated plates as usual.

For in vivo studies, 10-12 µl of the Jagged-Fc/anti-Fc complex, or the anti-Fc antibody alone as a control, were injected into 6 sites of individual tibialis anterior muscles. Jagged-Fc alone (injected 48 hrs after injury) promoted similar inhibition of regeneration as did the Jagged-Fc/anti-Fc complex. To test for the effects of forced Notch activation, 10-12 µl of a 1:4 dilution of the anti-Notch-1 antibody supernatant was injected into 6 sites of individual tibialis anterior muscles. In those cases, hamster IgG at the corresponding concentration was used as a negative control. The quantitative analysis was performed by analyzing the effectiveness of regeneration of the injury induced by the needle itself. As a measure of regeneration efficacy, we counted the number of centrally-nucleated regenerating myotubes 5 days after the injury in muscles from mice of different ages having received either Jagged-Fc or anti-Notch-1 antibodies, or respective controls. The reproducibility and reliability of this quantitation is evident by the small standard deviations in control young muscle and control aged muscle.

Statistical Analysis. For quantitation of all studies, a minimum of 3-4 replicates was done for each condition of the experiment. Data are presented as means and standard deviations. Comparisons among groups were all done using analysis of variance (ANOVA). Differences were deemed to be statistically significant for p values of <0.05.

Example 2

Rejuvenation of Tissue Regeneration Through Parabiosis

Among the prominent age-related changes in tissues is the decline of regenerative potential. This regenerative potential is mediated by tissue-specific stem or progenitor cells. In skeletal muscle, these cells (satellite cells) depend on the Notch signaling pathway for their activation and lineage progression. In old muscle, this pathway fails to be triggered after injury. However, forced activation of Notch restores satellite cell activation and tissue regeneration. To examine the influence of circulatory factors on aged muscle regeneration and Notch pathway activation, we performed heterochronic parabioses between young and old mice, where the circulatory system is shared. Strikingly, this restored Notch signaling and regeneration of aged muscle. In addition, heterochronic parabioses enhanced proliferation of aged hepatocytes with restoration of the cEBP-α/Brm cell cycle regulatory complex, and promoted neurogenesis in the hippocampus in aged brains. These results demonstrate that molecular cues for stem cell activation are modulated by systemic factors that change with age, and that the loss of regenerative potential of aged stem and progenitor cells is reversed by modifying the systemic environment.

To examine the contribution of the systemic environment to tissue regeneration, an experimental system in which the regenerating tissues of an aged animal could be exposed to the systemic factors of a young animal (and vice-versa) by virtue of a parabiotic pairing of two mice was established. In parabiosis, the peripheral circulatory system becomes shared between joined animals.

Figure 8:
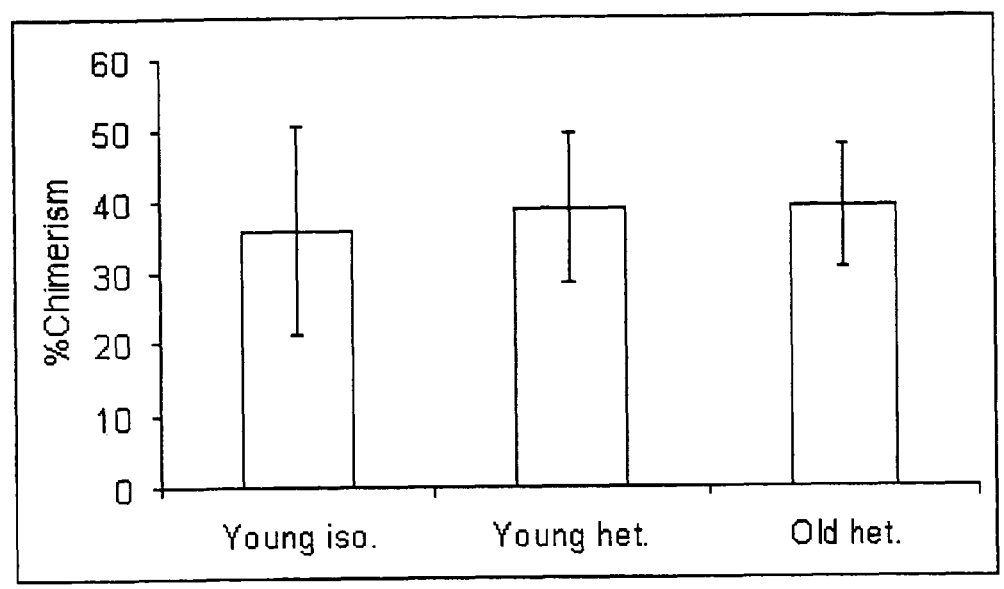
FIG. 8. Blood chimerism between parabiosed partners. Shown are the average and standard deviation of percent blood cells shared between parabiosed partners as determined by the Ly5.2 and eGFP markers after 5 weeks.
Figure 9:
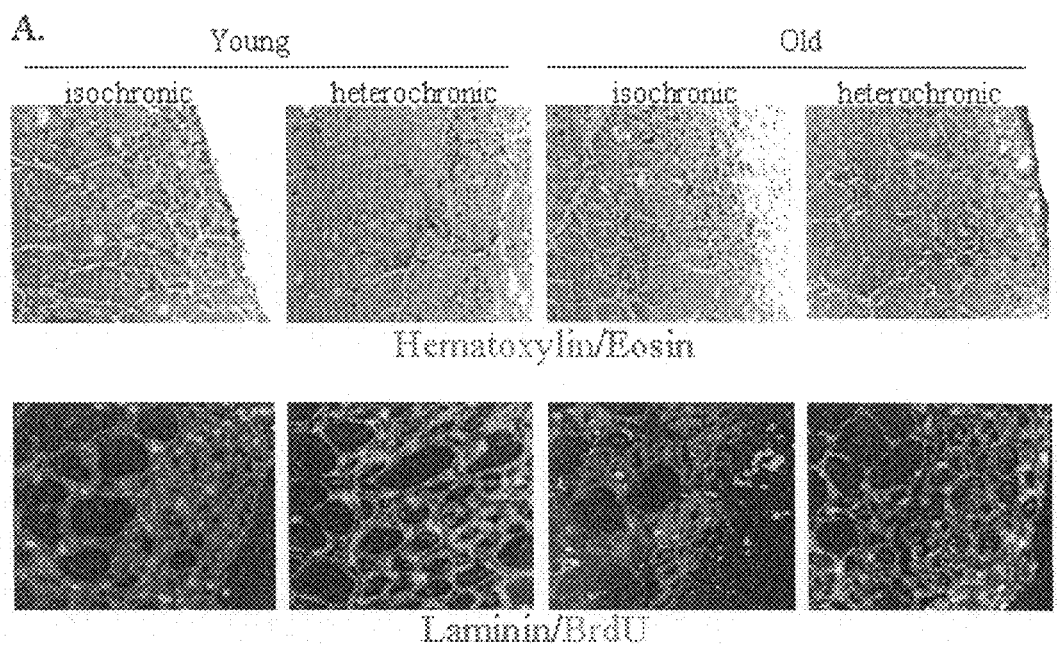
FIG. 9A-9B. Parabiosis to young restores muscle regeneration in old. 9A. (Top) Hematoxylin and eosin staining of sections from muscle 5 days after injury from isochronic and heterochronic parabionts. (Bottom) Immunostaining for BrdU (green) and laminin (red) of sections from the injured muscle. Whereas old muscle regenerated poorly in isochronic parabionts, the regeneration was markedly enhanced by heterochronic pairing to young animals. This is evidenced by the presence of fields of regenerating, centrally-nucleated myotubes and numerous BrdU+ nuclei in those myotubes, just as in young isochronic and heterochronice parabionts. (Representative fields from muscles from 4 individual pairings under each condition). 9B. Satellite cell activation after muscle injury. After 5 weeks of parabiosis muscle fibers were isolated and cultured ex-vivo for 1 day to activate satellite cells. Satellite cells were prepared and analyzed by flow cytometry for the expression of CD34 and Delta, with the population of Delta$^{hi}$/CD34⁺ cells representing activated satellite cells. Data are presented as average±standard deviation (n=3-6, p=0.01 between old iso- and heterochronic parabionts, p=0.17 between young iso- and heterochronic parabionts and p=0.30 between young and old hetoerochronic parabionts)
Figure 9:
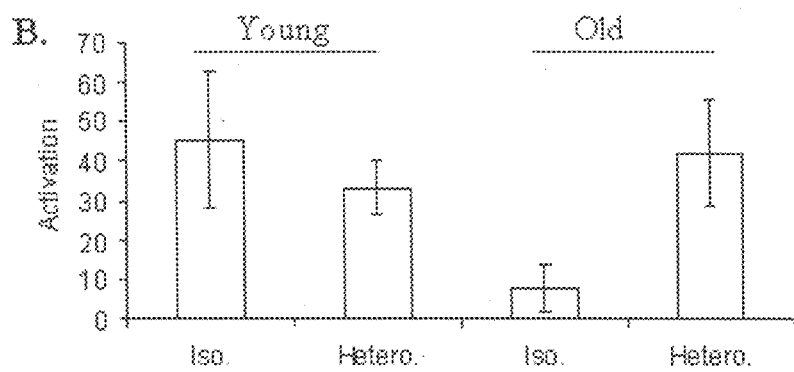
Figure 10:
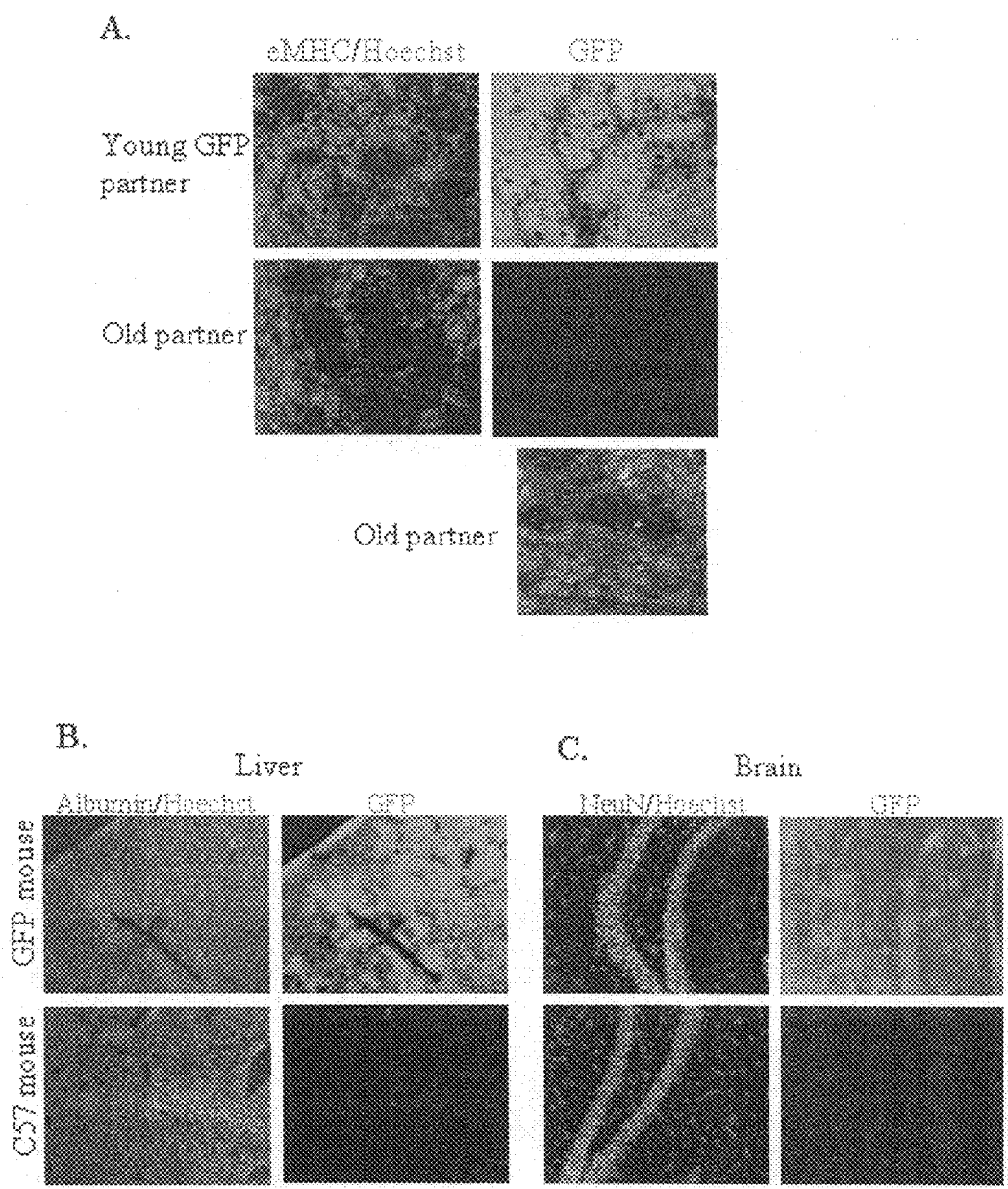
FIG. 10A-10C. Regenerated muscle, liver and neural cells in parabionts are endogenously derived. 10A. Old C57Bl/6 mice were parabiosed to young act:eGFP partners for 5 weeks. Muscle was injured, allowed to heal for 5 days, and then dissected and cryosectioned. Embryonic myosin heavy chain (eMHC) immunostaining (red) indicates regenerating myofibers. Hoechst (blue) labels all nuclei. No GFP⁺ fibers (green) were seen in muscle from the old partner. Rare GFP⁺ cells were seen in the interstitial spaces between fibers (below). 10B. Livers from the same parabiotic pairings show occasional GFP⁺ cells the aged (GFP⁻) mice, but much fewer than liver proliferating cells seen near round portals. Albumin immunostaining (red) indicates hepatocytes. Hoechst (blue) labels all nuclei. 10C. Brains from the same parabiotic pairings were analyzed for GFP⁺ cells in the old (GFP⁻) partners. No GFP⁺ cells were detected in the studied region of the hippocampus. NeuN (red) is used as a neuronal marker, highlighting the characteristic pattern of the subgranular zone. Hoechst (blue) labels all nuclei.

The efficacy of tissue regeneration was examined after young and old mice were joined pair wise in heterochronic parabiosis, with isochronic pairs (young-to-young and old-to-old) used as controls. Blood chimerism is established in approximately 10 days. Young partners that were transgenic for GFP or expressed a particular CD45 allele (Ly5.2), allowed the confirmation of blood chimerism (FIG. 8). The use of GFP-transgenic mice as one member of a pair also allowed us to distinguish the cells from each animal participating in tissue regeneration. After 5 weeks of parabiosis, the hind limb muscles of each mouse were injured and BrdU was injected intra-peritoneally 2 days later to label proliferating cells. 5 days after injury, muscles were isolated and assessed for the extent of regeneration by tissue morphology and immunohistochemistry. There was robust regeneration of muscle in young mice in both isochronic and heterochronic parabioses, including successful satellite cell activation and generation of myoblasts to participate in muscle repair (FIG. 9A). In contrast, injured muscle from old isochronic parabionts showed a characteristic lack of regeneration typical of aged animals, with minimal new fiber generation. The few BrdU+ nuclei in the tissue were located outside of myofibers. Remarkably, parabiosis with a young mouse significantly enhanced the regeneration of muscle in the old partner (FIG. 9A). Importantly, the origin of the cells participating in the successful regeneration of aged muscle was unambiguously established as being from the aged member of the pair by the lack of GFP expression. The few GFP+ cells derived from the young partner and present at the site of the injury were mononucleated and located in the interstitial spaces, most likely being infiltrating leukocytes from the blood (FIG. 10A). This experiment indicates that the impaired regenerative potential of aged muscle can be improved by a modification of the systemic environment, being either an increase of positive, circulating factor(s) from the young mouse or a decrease of inhibitory factor(s) from the old mouse, or both.

To examine if this rejuvenation of aged muscle regeneration was due to a reversal of the age-related decline in Notch signaling, we analyzed the expression of the Notch ligand Delta in satellite cells isolated from resting or injured muscle of isochronic and heterochronic parabionts. The cells were analyzed by flow cytometry for the expression of the satellite cell marker, CD34, and the activation marker Delta. In young isochronic and heterochronic parabionts, injury induced the up-regulation of Delta in CD34+ satellite cells, while Delta induction was lacking in the old, isochronic parabionts (FIG. 9B), typical of the response of aged muscle. Remarkably, and consistent with the regeneration results above, satellite cells from the aged partners of heterochronic parabionts showed a similar up-regulation of Delta as satellite cells from the young partners (FIG. 9B), and from young mice not subjected to parabiotic pairings. There was at most a slight inhibition of Delta up-regulation in satellite cells from the young partner of the heterochronic parabionts compared to young isochronic parabionts (FIG. 9B). Thus, heterochronic parabiosis restored the molecular signals important for muscle regeneration.

We then examined other organs from aged mice subjected to heterochronic parabiosis for evidence of rejuvenation of regeneration. As in muscle, a progressive loss of regenerative potential with age is well documented in liver and in the brain. However, the processes of regeneration as studied in these tissues differ in several aspects from the injury response of skeletal muscle described above. While satellite cells in resting muscle are normally quiescent and their activation/proliferation is triggered by injury, in liver there is also an ongoing low level of regeneration that is dramatically enhanced by liver damage. Brain resident stem cells participate in continuous neurogenesis (production of neurons, astrocytes and oligodendrocytes) in the sub-granular and sub-ventricular zones of the hippocampus. Therefore, liver and brain are different models for how tissue-specific progenitor cells respond to the environment and participate in the tissue maintenance and repair that declines with age.

Figure 11:
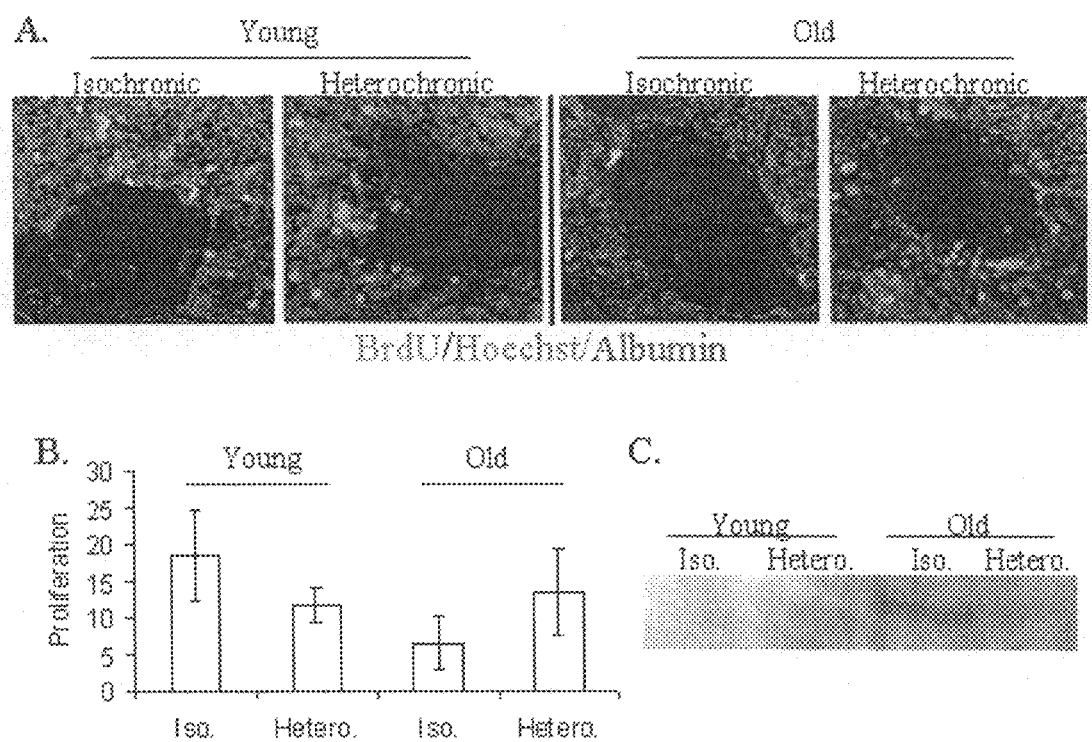
FIG. 11A-11C. Hepatocyte proliferation during parabiosis. 11A. BrdU was administered to 5 week parabionts at 5, 3 and 1 day before mice were sacrificed and livers were processed for immunofluorescence analysis. Sections were analyzed for proliferation by BrdU incorporation (green), liver cell marker by albumin staining (red) and all nuclei by Hoechst staining (blue). Mag.=40×. 11B. Quantification of hepatocyte proliferation. Immunostained sections as in panel "A" were analyzed for the number of BrdU$^+$/albumin$^+$ cells per section. Data are presented as means±SD (n=3-5 for each condition, p=0.16 between old iso- and heterochronic parabionts, p=0.07 between young iso- and heterochronic parabionts and p=0.67 between young and old heterochronic parabionts). 11C. Western blot analysis of protein extracts prepared from liver sections of isochronic or heterochronic parabionts. Extracts were immunoprecipitated with an anti-cEBP-α antibody, and probed with an anti-Brm antibody. The cEBP-α/Brm complex seen prominently in the livers of old isochronic parabionts and typical of aged livers, was significantly reduced in the livers of old heterochronic parabionts (n=3).

To identify proliferating stem and progenitor cells in those tissues, mice received 3 injections of BrdU (one injection every other day) after parabiosis had been established for 5 weeks. Liver was isolated from heterochronic and isochronic parabionts and sections were analyzed by immunofluorescence using anti-BrdU and anti-albumin antibodies. Young isochronic parabionts showed proliferating hepatocytes, and old isochronic parabionts displayed less than half the hepatocyte proliferation seen in the young (FIG. 2A), typical of aged mice. Similar to what was seen in the muscle system, parabiosis to a young partner increased the basal hepatocyte proliferation in old parabionts (FIG. 2A). Consistent with previous observations, very few partner-derived, GFP+ hepatocytes were detected in the non-transgenic parabiotic partners (FIG. 10B), indicating that virtually all of the proliferating hepatocytes were endogenous to the tissue and not derived from circulating stem cells. While heterochronic parabiosis reproducibly enhanced cell proliferation in the old livers, a reduction of cell proliferation was detected in young livers after heterochronic parabiosis to old mice (FIG. 11B). This may reflect a dilution of either a stimulating factor from the young partner, or an inhibitory factor from the old, in the shared circulatory pool.

The age-related defect in hepatocyte proliferation was recently linked to the formation of an age-specific complex of cell-cycle regulators that inhibit the E2F-driven gene expression and co-immunoprecipitate with cEBP-α. One of the proteins present in this complex in old livers, but not young, is an evolutionary conserved chromatin remodeling factor, Brahma (Brm), which plays a role in *D. melanogaster* organogenesis. We tested whether the rejuvenation of aged liver hepatocyte proliferation was related to a restoration of the levels of cEBP-α/Brm back to that seen in young animals. As shown in FIG. 11C, the cEBP-α/Brm protein complex is easily detected in liver extracts from isochronic old parabionts, and not in the liver extracts from isochronic young parabionts, similar to the data obtained in rodents not subjected to parabiosis. Strikingly, the formation of a cEBP-α/Brm complex was diminished in liver extracts from old heterochronic parabionts (FIG. 11C), this being a characteristic of young hepatocytes that proliferate more readily. Interestingly, the complex formation was slightly elevated in young heterochronic parabionts compared to young controls, also consistent with the modest inhibition of hepatocyte proliferation in young heterochronic parabionts (FIG. 11B). These data strongly suggest that, as with muscle precursor cells, the young systemic milieu restored a younger profile of molecular signaling to the aged hepatocytes. Notably, heterochronic parabiosis affected distinct signal transduction pathways in old muscle (Delta/Notch) and old liver (cEBP-α/Brm) that are altered by the aging process and required for tissue regeneration.

Figure 12:
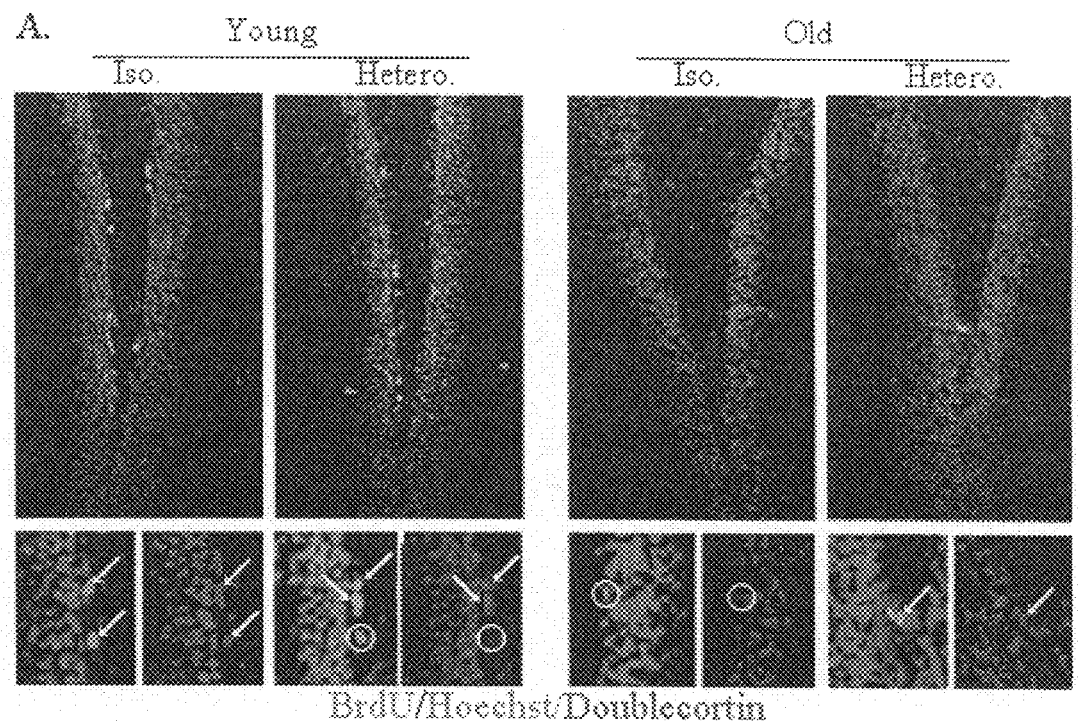
FIG. 12A-12B. Neurogenesis during parabiosis. 12A. BrdU was administered to 5 week parabionts at 5, 3 and 1 day before mice were sacrificed and brains were processed for immunofluorescence analysis. (Top panels) Sections through the dentate gyrus of the hippocampus were immunostained for BrdU to identify proliferating cells (green), Doublecortin to identify new neuronal cells (red) and Hoescht to show all nuclei (blue). (Bottom panels) Higher magnification of regions from top panels. Arrows indicate proliferating neurons (BrdU$^+$/Doublecortin$^+$), where circled areas indicate non-neuronal proliferating cells (BrdU$^+$/Doublecortin$^-$). 12B. Quantification of neurogenesis. Sections as in panel "A" were analyzed for the total numbers of proliferating neuronal cells (BrdU$^+$/Doublecortin$^+$), found sectioning through 450 micrometers of the dentate gyrus. Note that the scales for the young and old animals are different because of the marked reduction in basal neurogenesis in the brains of old mice compared to those of young mice. (n=3 for each condition, p=0.02 between old iso- and heterochronic parabionts, p=0.09 between young iso- and heterochronic parabionts).
Figure 12:
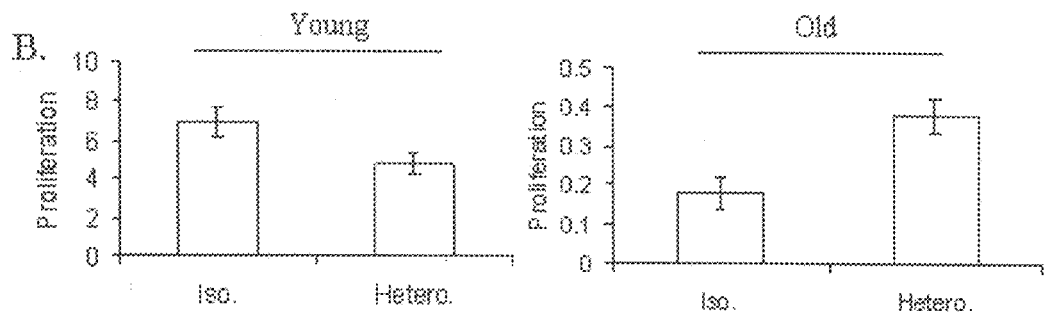

Finally, we analyzed basal neurogenesis during heterochronic parabiosis. As expected from data obtained in animals not subjected to parabiosis, generation of BrdU+ neural progenitor cells was relatively robust in the subgranular zone of hippocampus in young isochronic parabionts (FIG. 12). Most of the BrdU+ cells in that region expressed an early neuronal marker, doublecortin. In contrast, very few BrdU+/doublecortin+ cells were present in the subgranular zone of the hippocampus in old isochronic parabionts (FIG. 12). However, heterochronic parabiosis resulted in a significant increase in neurogenesis in the aged hippocampus (FIG. 12). As has been observed, no GFP+cells were detected in the studied regions of brains derived from non-transgenic partners of GFP parabionts (FIG. 10C), confirming that the enhancement in neurogenesis in the old hippocampus occurred from the aged resident stem cells. As with liver, there was a mild inhibitory effect by heterochronic parabiosis on the regenerative activity in the young partner, where neurogenesis was reduced slightly compared to the isochronic controls (FIG. 12B). The magnitudes of the effects of heterochronic parabiotic were smaller in the brain then in the liver or skeletal muscle.

These experiments demonstrate the presence of systemic factors in the circulation that can modulate molecular signaling pathways critical to the activation of organ stem cells and to tissue regeneration, and that the systemic milieu of a young animal is one that promotes successful regeneration while that of an older animal either fails to promote or actively inhibits successful tissue regeneration.

The results of this work also demonstrate that decline of tissue regenerative potential with age is not permanent and can be reversed through the modulation of systemic factors. Importantly, heterochronic parabiosis restored the signal transduction required for tissue repair in the old animals, suggesting that the molecular cues of stem cell activation are modulated by the systemic factors. Such a conclusion is consistent with the idea that adult stem cells maintain much if not all of their intrinsic regenerative potential even when old, but that it is the age-related changes in systemic factors that preclude activation of these cells and interfere with productive tissue repair.

Materials and Methods

Animal Strains and Parabiosis. Young (2-4 month) C57Bl/6 mice containing the actin:eGFP transgene and 5.2 Ly allele were from the Weissman Laboratory. Old (22-26 month) C57Bl/6 mice were obtained from the National Institutes of Aging or aged in our own colonies; young C57Bl6 mice were obtained from Jackson Laboratories (Bar Harbor, Me.). Animals were housed and handled in accordance with the guidelines of Veterinary Medical Unit of the VA Palo Alto Health Care System and the Administrative Panel on Laboratory Animal Care of Stanford University. Parabiosis was performed as published by Wagers et al. (2002) *Science* 297, 2256-2259.

Reagents. Antibodies to Delta, cEBP, and doublecortin were purchased from Santa Cruz Biotechnology (Santa Cruz, Calif.), to CD34 and Brm from Beckton-Dickinson (San Jose, Calif.), and to albumin and laminin from Sigma (St. Louis, Mo.). The anti-BrdU staining kit was purchased from Beckton-Dickinson and the bromodeoxyuridine labeling reagent was from Zymed (South San Francisco, Calif.). Fluorophore-conjugated secondary antibodies for flow cytometry and immunofluorescence were obtained from Caltag (Burlingame, Calif.) and used as previously described by Conboy & Rando (2002) *Dev. Cell* 3, 397-409.

Muscle Injury.

Satellite cell activation. In order to reproducibly and robustly induce activation of satellite cells, hindlimb muscles (gastrocnemius, biceps femoris and quadriceps), were dissected, digested into bulk fibers and cultured over night ex vivo as described by Conboy et al. (2003) *Science* 302, 1575-1577.

Tissue response to injury. In order to analyze molecular changes in situ in response to injury, a small focal injury was made by an application of dry ice for 5 seconds directly to the tibialis anterior muscle. This produces a very reproducible "wedge" injury in the muscle with a discrete border between uninjured and injured muscle, and this border remains clear and distinct during the regeneration of the injured tissue.

Satellite cell isolation. Satellite cells were purified from bulk fibers. The resulting preparation contained mononucleated cells that were >95% CD34+, m-Cadherin+ satellite cells, which could be distinguished from remaining debris on FACS analysis by the characteristic forward scatter and side scatter properties of cells.

Immunofluorescence. Muscles were dissected and embedded for cryostat sectioning as previously described. Tissue sections were washed in staining buffer (1% FBS in PBS) and blocked for 30 min in staining buffer containing 0.25% Triton X-100. Primary and isotype-matched control antibodies were diluted in staining buffer (1 µg/100 µl). Sections were stained for 2 hours at room temperature, washed in staining buffer, and incubated with fluorochrome-conjugated secondary antibodies with Hoechst dye for 1 hour at room temperature. Cells in culture were fixed in 6-well plates for immunofluorescence analysis, and all procedures were as previously described by Conboy and Rando, supra.

Fluorescent activated cell sorting (FACS). Cells were live or fixed with 4% paraformaldehyde. Fixed cells were stained with primary antibodies or with isotype-matched control antibodies (1 µg in 100 µl) for 1 hour at room temperature (30 minutes on ice for live cells), followed by incubation with fluorochrome-labeled secondary antibodies (1:200-1:500 dilutions) for 1 hour at room temperature. Cells were analyzed by FACScan (Beckton-Dickinson) using compensation for green and red fluorescence and doublet discrimination parameters.

Western Blotting. For Western analysis, cells and myofiber explants were detached and lysed in RIPA buffer (50 mM Tris-HCl, 1 mM EDTA, 1 mM EGTA, 150 mM NaCl, 1% NP-40) containing 90 µg/ml PMSF, 20 µg/ml aprotinin and 20 µg/ml leupeptin (Sigma). Immunoblotting was performed as previously described by Conboy & Cyert (2000) *Mol. Biol. Cell* 11, 2429-2443.

Statistical Analysis. A minimum of 3 replicates was done for each experiment. Data are presented as means and standard deviations. Comparisons among groups were all done using Student's t-test assuming two-tailed distribution and unequal variances.

Example 3

Regeneration Inhibiting Factors

Figure 13:
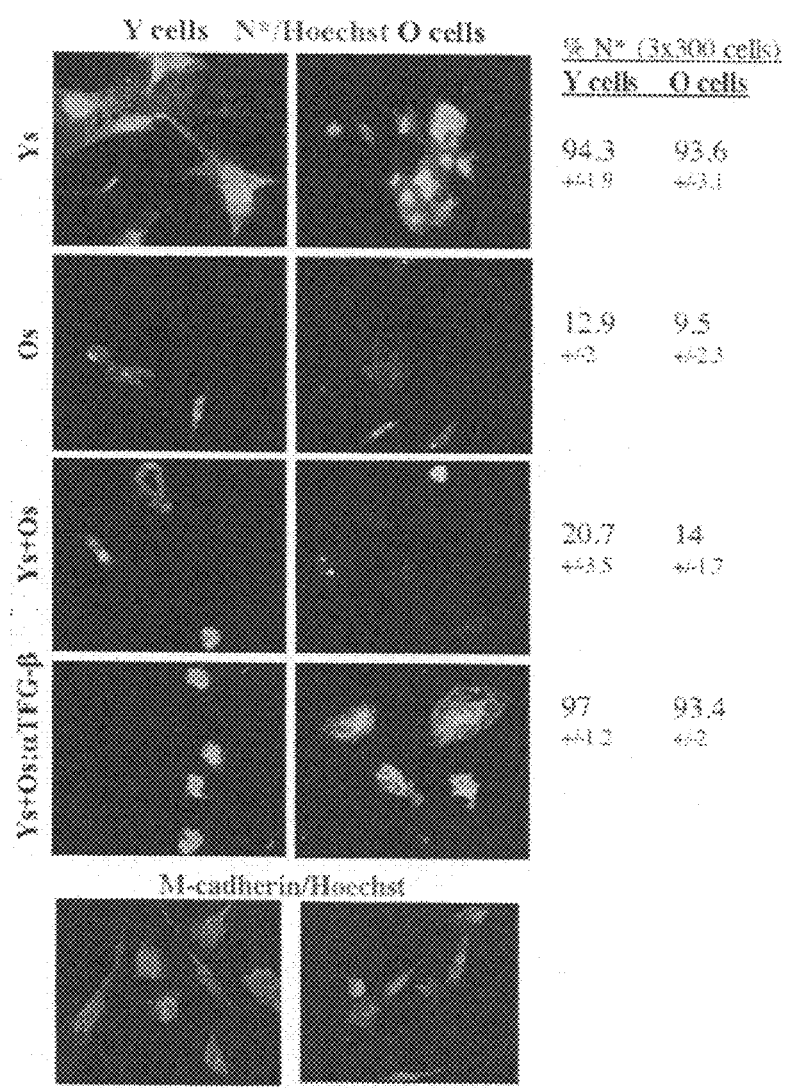
FIG. 13. Satellite cells from young mice (Y) and satellite cells from old mice (O) were cultured in the presence of 10% serum from young animals (Ys); old animals (Os); a combination of young and old serum (Ys+Os); or the combination in the presence of neutralizing antibodies specific for TGF-β. The percent of cells having activated Notch (N*) is shown for each of the culture conditions.

The activation status of Notch was determined in freshly isolated young and old satellite cells cultured in the presence of young or old mouse serum. As shown in FIG. 13, at 10% serum, the age of the serum clearly determined the activation status of Notch in the satellite cells.

The levels of active nuclear Notch were diminished in the presence of old serum in both young and old satellite cells, and young serum restored the activation of Notch to the aged satellite cells. The inhibitory effect of aged serum on the activation of Notch in young cells shown here are more pronounced than in experiments when the levels of the serum were lower, suggesting a molecular threshold for the inhibitory activity present in the old serum.

As described above, virtually all young and old cells express the satellite cell marker, M-Cadherin. To test for an inhibitory component in old serum, satellite cells were cultured in a mixture of young and old sera (Ys+Os), 5% each, with the total % of serum being equal to Ys or Os (10%). As shown in FIG. 13, (Ys+Os), the old serum clearly dominated over the young serum, strongly suggesting that the young serum has positive effects on the activation of Notch largely because the inhibitory influence of the old serum is not present.

Figure 14:
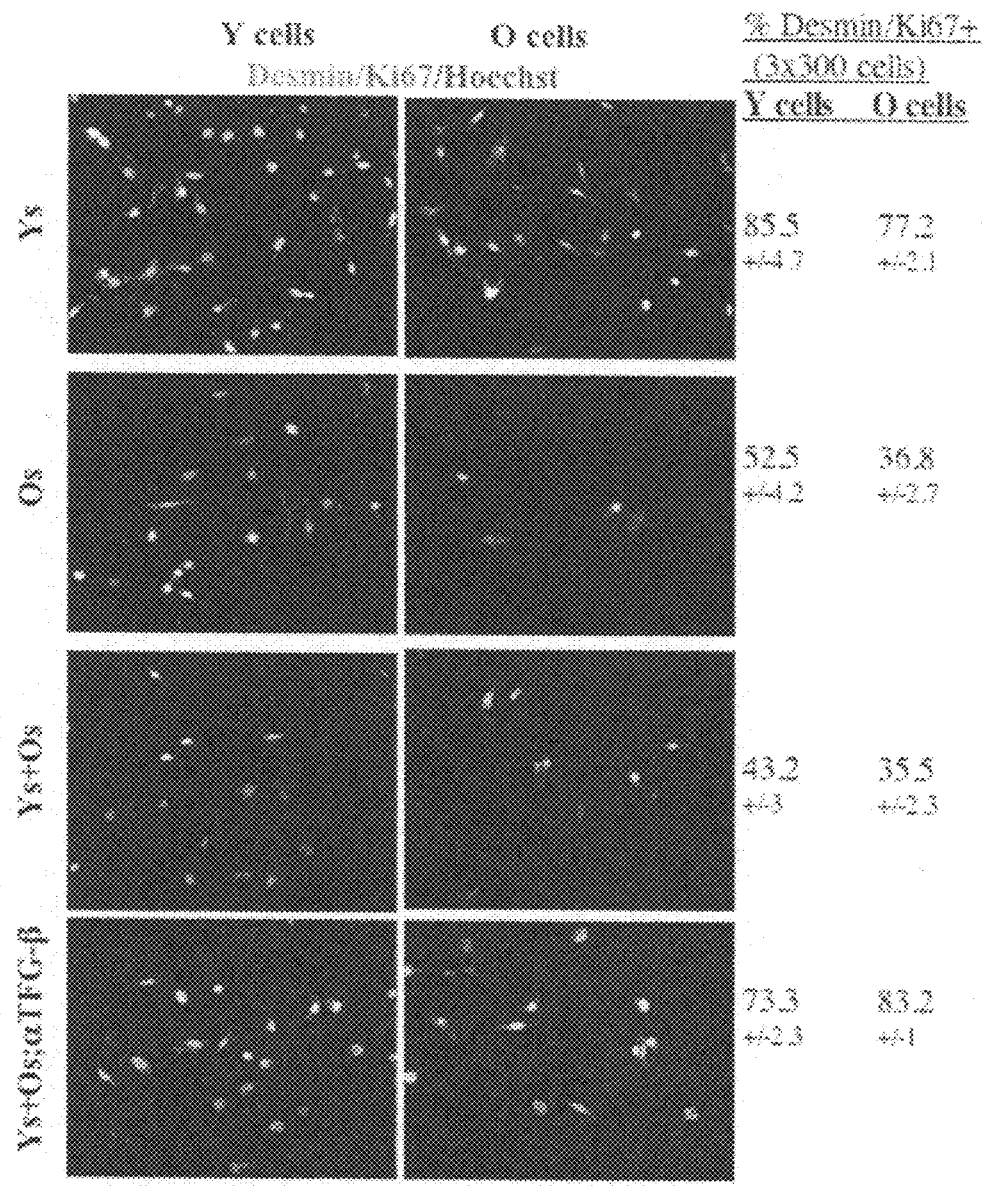
FIG. 14. Satellite cells were cultured under conditions as described for FIG. 13, and are evaluated for the presence of desmin/Ki67, which is indicative of the regenerative potential of the cells.

It was then tested whether the inhibitory component in the old serum that negatively affects the activation of Notch in satellite cells belongs to the TGFβ protein family. As shown in FIG. 14 (Ys+Os; αTGFβ1), the presence of a pan-neutralizing antibody to TGF-β (1D11, R&D) relieves the inhibitory effect of the old serum on the activation of Notch in both young and old cells, demonstrating that at least some of the inhibitory influence is associated with the TGF-β protein family. Importantly, aged satellite cells cultured with a mixture of young and old sera failed to activate Notch unless TGF-β was neutralized, suggesting that the attenuation of TGF-β signaling is necessary for the restoration of this regeneration-specific molecular pathway in old cells by the young serum. This pan-neutralizing antibody also resulted in a slightly higher activation of Notch, when young or old cells were cultured in old serum alone.

Since activation of Notch is the key molecular determinant of the satellite cell regenerative potential that is lost with age, it was tested whether the age of the serum also determines the satellite cell regenerative capacity and specifically, how efficiently the activated satellite cells generate proliferating myogenic progenitor cells, or myoblasts. As shown in FIG. 14, in perfect correlation with the activation status of the Delta-Notch pathway shown in FIG. 13, the age of serum determined the satellite cell regenerative potential and a high percent of old serum inhibited the regenerative potential of young satellite cells. Namely, the percent of desmin+/Ki67+ proliferating myoblasts increased by ~2 fold in the presence of young mouse serum in both young and old cultures. In addition, there were 2-3 times fewer total cells generated in the presence of aged serum (FIG. 2).

Consistent with the effects on Notch activation, old serum also inhibited the satellite cell regenerative potential even when young serum was present, but neutralizing TGF-β removed such inhibition. Therefore, not only the regeneration-specific molecular signaling, but also the satellite cell regenerative potential are dependant on the age of the systemic milieu, and the inhibitory component in aged serum that affects the ability of satellite cells to generate proliferating myoblasts is associated with the TGF-β protein family. While noticeable, the inhibitory effects of old serum were much less pronounced when it was mixed with young serum in vivo, in the shared common circulation. These results suggest that the inhibitory factors present in the old circulation have been either cleared or functionally neutralized by the young animal during the first 5 weeks of heterochronic parabiosis that preceded the data collection and analysis.

These data demonstrate that old serum inhibits Delta-Notch signaling and satellite cell regenerative potential and that these negative effects are associated with the TGF-β protein family.

What is claimed is:

1. A method for regeneration after injury of skeletal muscle tissue in an aged human or mouse, the method comprising:
   contacting skeletal muscle tissue having an age related loss of ability to form new muscle tissue from satellite cells with a composition comprising Notch ligand Delta or an antibody that specifically binds to Notch 1 and activates the Notch signaling pathway, to induce said muscle satellite cells to proliferate, wherein the progeny of said muscle satellite cells undergo differentiation to cells of said skeletal muscle tissue to regenerate said skeletal muscle tissue.

2. The method according to claim 1, wherein said antibody that specifically binds to Notch 1 is formulated with a pharmaceutically acceptable excipient.

3. The method of according to claim 1, wherein said antibody composition comprises a combination of said Notch ligand Delta or antibody that specifically binds to Notch 1 and a neutralizing antibody specific for TGF-β.

4. The method according to claim 1, wherein said antibody that specifically binds to Notch 1 is administered systemically.

5. The method according to claim 1, wherein said antibody that specifically binds to Notch 1 is administered locally.

6. The method according to claim 1, wherein said antibody that specifically binds to Notch 1 specifically binds to human Notch 1.

* * * * *